United States Patent
Predick et al.

(10) Patent No.: US 10,149,671 B2
(45) Date of Patent: Dec. 11, 2018

(54) RETRACTOR WITH MODULAR HANDLES

(71) Applicant: Life Spine, Inc., Huntley, IL (US)

(72) Inventors: Daniel Predick, Chicago, IL (US); Michael S. Butler, St. Charles, IL (US)

(73) Assignee: Life Spine, Inc., Huntley, IL (US)

( * ) Notice: Subject to any disclaimer, the term of this patent is extended or adjusted under 35 U.S.C. 154(b) by 0 days.

(21) Appl. No.: 15/207,026

(22) Filed: Jul. 11, 2016

(65) Prior Publication Data

US 2016/0317137 A1 Nov. 3, 2016

Related U.S. Application Data

(63) Continuation-in-part of application No. 14/874,073, filed on Oct. 2, 2015, which is a continuation-in-part of application No. 13/720,800, filed on Dec. 19, 2012, now Pat. No. 9,386,916.

(60) Provisional application No. 61/577,857, filed on Dec. 20, 2011.

(51) Int. Cl.
*A61B 17/02* (2006.01)

(52) U.S. Cl.
CPC .............................. *A61B 17/0206* (2013.01)

(58) Field of Classification Search
CPC .................................................. A61B 17/0293
See application file for complete search history.

(56) References Cited

U.S. PATENT DOCUMENTS

| | | | | |
|---|---|---|---|---|
| 530,728 A | * | 12/1894 | Sherbrook | A61B 1/32 600/224 |
| 3,509,873 A | * | 5/1970 | Karlin | A61B 17/02 600/226 |
| 4,065,941 A | * | 1/1978 | Aoki | F16D 3/207 464/115 |
| 7,335,207 B1 | * | 2/2008 | Smith | A61F 2/4609 606/80 |
| 2004/0049101 A1 | | 3/2004 | Phillips et al. | |
| 2005/0215866 A1 | | 9/2005 | Kim | |
| 2007/0049930 A1 | * | 3/2007 | Hearn | A61B 17/66 606/56 |
| 2007/0203399 A1 | | 8/2007 | Gephart et al. | |
| 2007/0238932 A1 | | 10/2007 | Jones et al. | |
| 2010/0154604 A1 | * | 6/2010 | Su | B25B 13/481 81/450 |
| 2010/0222644 A1 | * | 9/2010 | Sebastian | A61B 17/0206 600/228 |
| 2011/0130793 A1 | | 6/2011 | Woolley et al. | |
| 2011/0301423 A1 | * | 12/2011 | Koros | A61B 17/02 600/229 |

(Continued)

FOREIGN PATENT DOCUMENTS

WO WO2015160343 * 4/2014 ............. A61B 17/02
WO WO 2015/134367 A1 9/2015

*Primary Examiner* — Samuel Hanna
(74) *Attorney, Agent, or Firm* — Foley & Lardner LLP

(57) ABSTRACT

A retractor assembly includes a base; a first side arm assembly coupled to a first side of the base and configured to translate relative to the base along a first direction; a second side arm assembly coupled to a second side of the base and configured to translate relative to the base along the first direction independent from the first side arm assembly; and a central arm assembly coupled to a center portion of the base and configured to translate relative to the base along a second direction different from the first direction.

7 Claims, 24 Drawing Sheets

(56) References Cited

U.S. PATENT DOCUMENTS

| | | | |
|---|---|---|---|
| 2014/0024900 A1* | 1/2014 | Capote | A61B 17/0206 600/214 |
| 2015/0230787 A1 | 8/2015 | Friedrich et al. | |
| 2015/0250467 A1* | 9/2015 | Higgins | A61B 17/0206 600/215 |
| 2015/0305731 A1 | 10/2015 | Friedrich et al. | |
| 2015/0313585 A1 | 11/2015 | Abidin et al. | |

\* cited by examiner

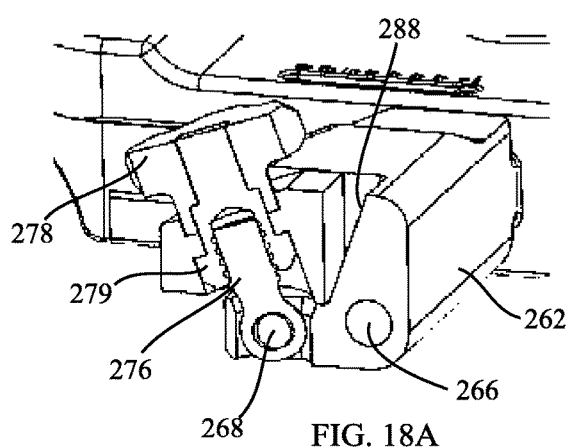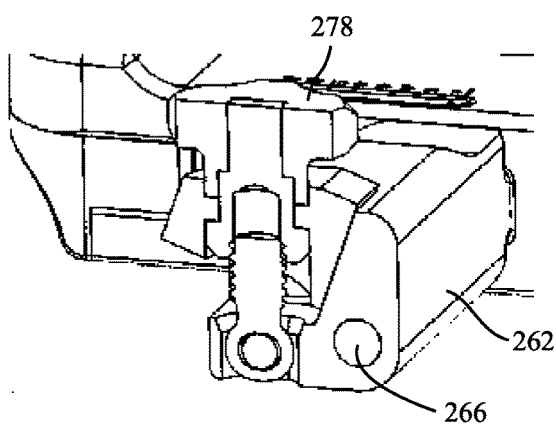
FIG. 18A  FIG. 19A
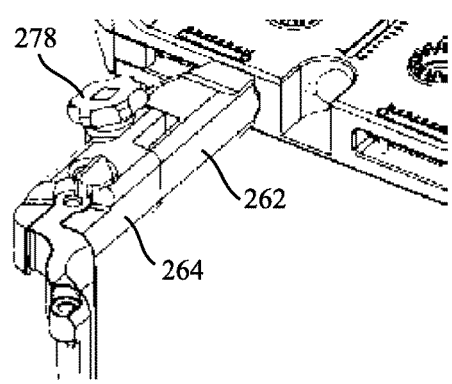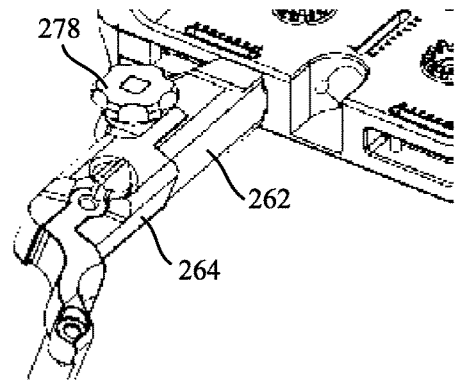
FIG. 18B  FIG. 19B

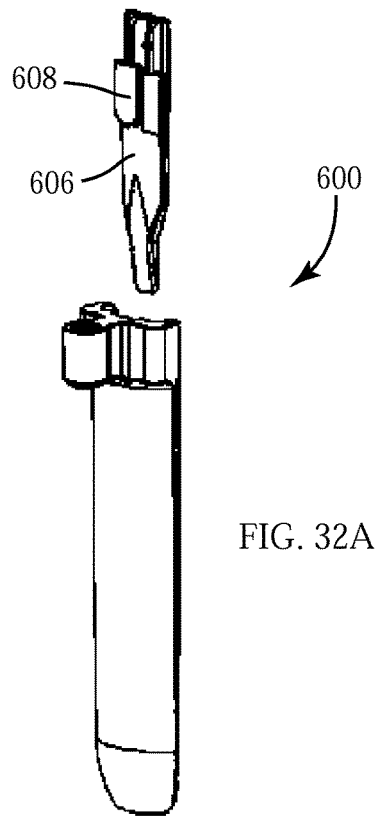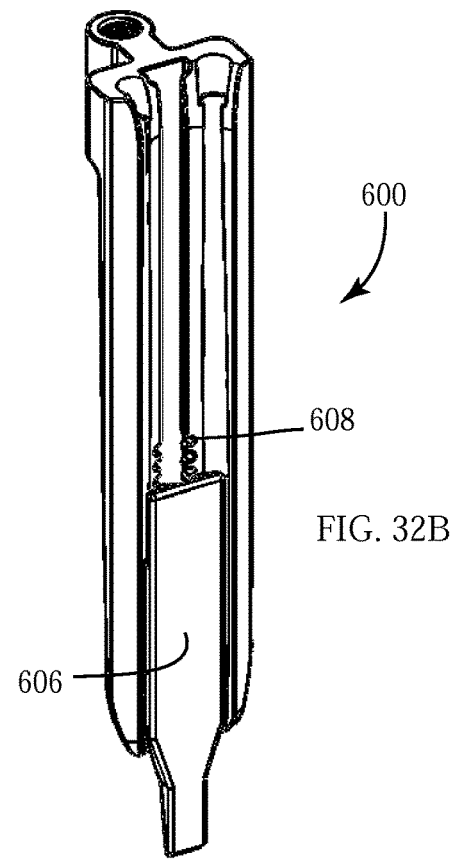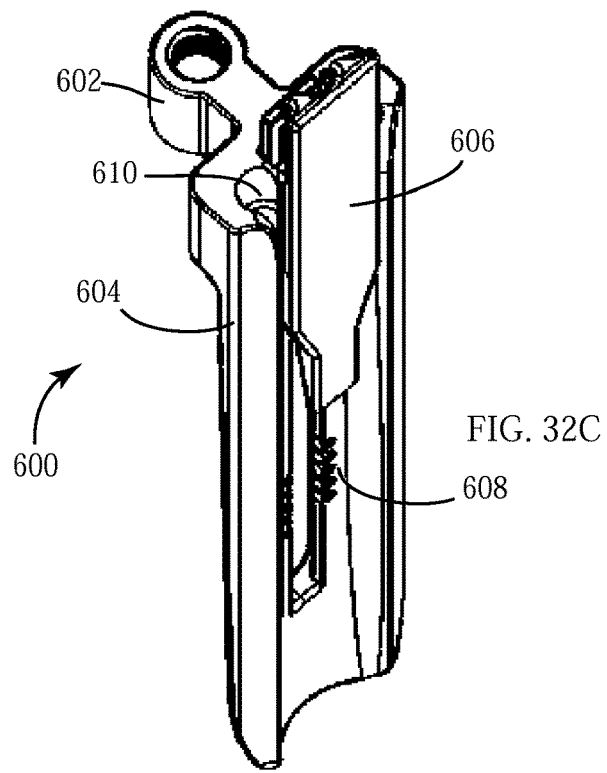
FIG. 32A
FIG. 32B
FIG. 32C

RETRACTOR WITH MODULAR HANDLES

CROSS-REFERENCE TO RELATED PATENT APPLICATIONS

This application is a continuation-in-part of application Ser. No. 14/874,073, filed Oct. 2, 2015, which is a continuation-in-part of application Ser. No. 13/720,800, filed Dec. 19, 2012, which claims the benefit of Provisional Application No. 61/577,857 filed Dec. 20, 2011. The entire contents of all of these applications are incorporated herein by reference.

BACKGROUND

The present invention relates to surgical devices for retracting anatomy to provide exposure of an operating site, and more particularly, to retraction apparatus providing improved access to a surgical site for a spine procedure.

Surgical procedures typically require the use of a retractor to hold anatomies and/or tissues out of the way from the incision down to the actual surgical site. In the case of posterior spinal surgery for implanting various spine fixation components and/or other spinal orthopedic devices, it is necessary to retract different tissue types including large and strong paraspinal muscles in order to get to the actual surgical site. In order to accomplish this goal, spinal retractors have been developed that hold back the desired anatomy of a spinal surgical site and is fixed relative to the patient either directly or indirectly.

Many different types of spinal retractors are currently available many of which use retractor blades—a part of the distraction mechanism of the spinal retractor that enters the site of the incision and physically holds the anatomy apart. The retractor blades can be attached to a frame at an angle such as about 90 degrees from horizontal (i.e. generally vertical) or as to have a variable angle. However, current spinal retractors have various deficiencies. For instance, fixed angle retractor blade configurations limit flexibility of the spinal retractor, including loss of surgical site precision and overall stabilization. The variable angle retractor blade configurations lack preciseness and flexibility in retractor blade positioning.

It is therefore evident from the above that there is a need for an improved spinal retractor that can overcome the deficiencies of current spinal retractors. It is also evident from the above that there is a need for an improved spinal retractor which provides enhanced preciseness and flexibility in retractor blade positioning. It is furthermore evident that there is a need for an improved spinal retractor as aforementioned which also allows for instrument and/or component retention and positioning by the retractor blade assembly.

SUMMARY

The present disclosure relates to a spinal retractor for spinal surgeries providing improved preciseness and stability in positioning, tissue distraction, and surgical site access. The spinal retractor utilizes adjustable and lockable translating arms with angulating blades to provide a stable surgical site finestra and the adjustable retraction of surgical site tissue.

The present spinal retractor is a three blade retractor that allows triangulated medial/lateral and cephalad/caudal tissue retraction for spinal surgeries via the adjustably lockable translating arms. A medial/lateral translating arm with an angularly adjustable retraction blade co-acts and cooperates with angularly adjacent first and second cephalad/caudal translating arms with angularly adjustable retraction blades for tissue retraction and surgical site access.

The spinal retractor includes a plate having a medial/lateral adjustment system adjustably holding the medial/lateral translating arm, a first cephalad/caudal adjustment system adjustably holding the first cephalad/caudal translating arm, and a second cephalad/caudal adjustment system adjustably holding the second cephalad/caudal translating arm. The translating arms each have a blade holder which provides angular adjustment of the blade. Angular adjustment of each blade along with medial/lateral and cephalad/caudal adjustment provides improved preciseness and stability in positioning, tissue distraction, and surgical site access.

Another embodiment relates to a retractor assembly, including a base, a first side arm assembly coupled to a first side of the base, a second side arm assembly coupled to a second side of the base, and a central arm assembly coupled to a center portion of the base. The first side arm is configured to translate relative to the base along a first direction based on rotation of a first drive shaft positioned at a first angle relative to the first direction. The second arm is configured to translate relative to the base along the first direction independent from the first side arm assembly and based on rotation of a second drive shaft positioned at a second angle relative to the first direction. The central arm is configured to translate relative to the base along a second direction different from the first direction based on rotation of a third drive shaft positioned at a third angle relative to the second direction.

Another embodiment relates to a retractor assembly, including a base, a first side arm assembly coupled to a first side of the base, a second side arm assembly coupled to a second side of the base, and a center arm assembly coupled to a central portion of the base. The first side arm assembly is configured to translate relative to the base along a first direction. The second side arm assembly is configured to translate relative to the base along the first direction. The center arm assembly is configured to translate relative to the base along a second direction different from the first direction. Each of the first side arm assembly, the second side arm assembly, and the center arm assembly is coupled to the base by an adjustment mechanism including a multi-joint joint assembly.

Another embodiment relates to a method of operating a retractor. The method includes placing a retractor into a desired position, wherein the retractor includes a frame, a first side assembly, a second side assembly, and a center assembly. The method further includes translating the first side assembly relative to the frame along a first threaded shaft and independent from the second side assembly and the center assembly by rotating a first knob coupled to the first threaded shaft via a first joint assembly. The method further includes translating the second side assembly relative to the frame along a second threaded shaft and independent from the first side assembly and the center assembly by rotating a second knob coupled to the second threaded shaft via a second joint assembly. The method further includes translating the center assembly relative to the frame along a third threaded shaft and independent from the first side assembly and the second side assembly by rotating a third knob coupled to the third threaded shaft via a third joint assembly.

Further aspects of the present disclosure will become apparent from consideration of the drawings and the following description of various embodiments. A person skilled in the art will realize that other embodiments are possible and that the details can be modified in a number of respects without departing from the inventive concepts disclosed herein. The following drawings and description are to be regarded as illustrative in nature and not restrictive.

BRIEF DESCRIPTION OF THE DRAWINGS

The features of the present disclosure will be better understood by reference to the accompanying drawings which illustrate various embodiments, wherein:

FIGS. 18A-19B illustrate various portions of a spinal retractor according to one embodiment.

FIGS. 31A-32C are various views of primary and secondary blades according to various exemplary embodiments.

Like reference numbers indicate the same or similar parts throughout the several figures.

Figure 1:
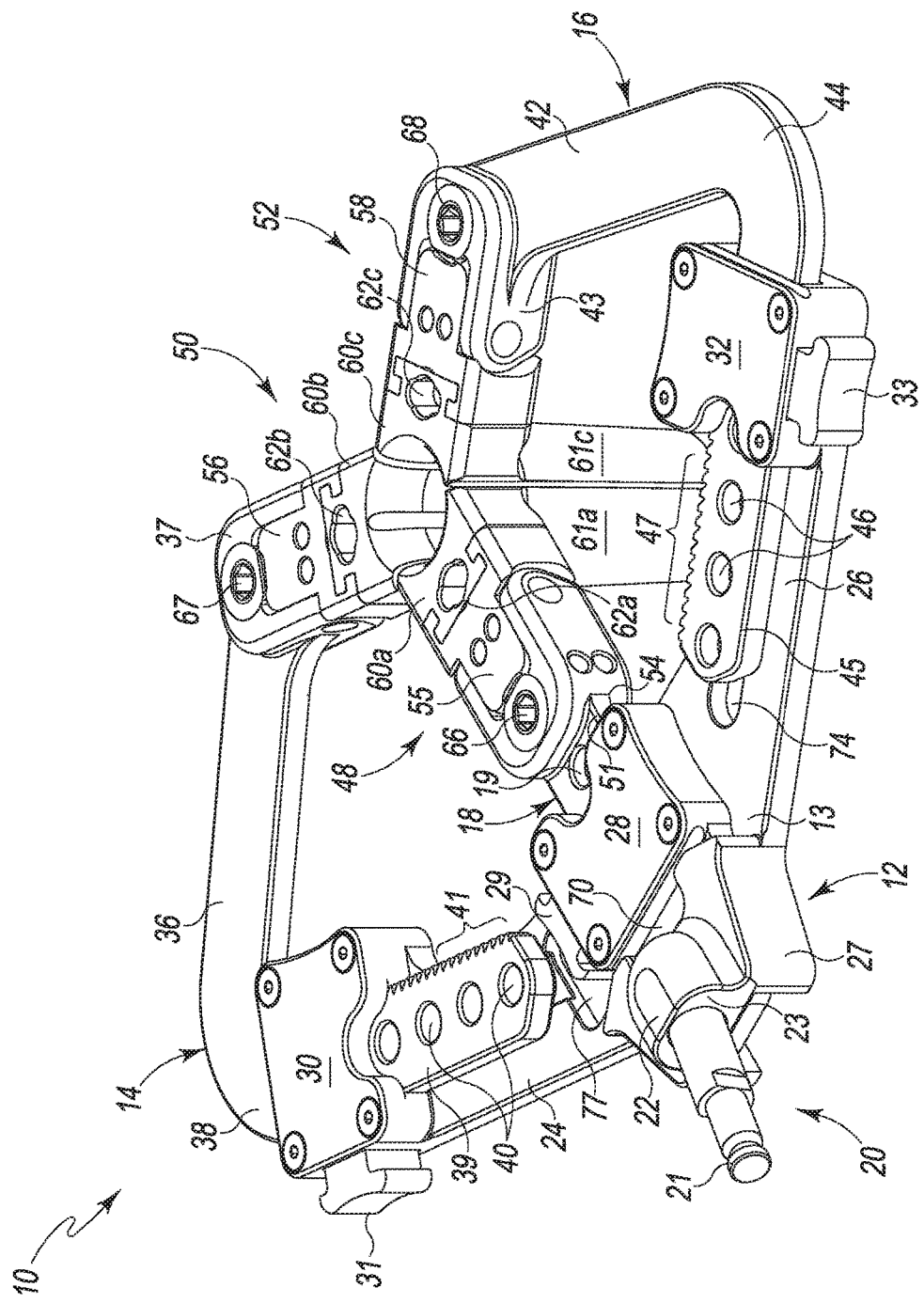
FIG. 1 is a topside view of a spinal retractor fashioned in accordance with the present principles, the spinal retractor shown in a closed position.

A description of the features, functions and/or configurations of the components depicted in the various figures will now be presented. It should be appreciated that not all of the features of the components of the figures are necessarily described. Some of these non-discussed features as well as discussed features are inherent from the figures. Other non-discussed features may be inherent in component geometry and/or configuration.

DETAILED DESCRIPTION

Reference is now made to FIGS. 1-5 which depict several views of a spinal retractor 10, fashioned in accordance with the present principles. The spinal retractor 10 is fashioned for use in anterior, posterior and lateral spinal surgeries or procedures, such as orthopedic implantation, vertebral fixation and vertebral stabilization, but may be used in other surgical procedures and orientations. The spinal retractor 10 is formed of an appropriate surgical material such as titanium, stainless steel, an alloy of same or the like.

The spinal retractor 10 has a body 12 characterized by a base, plate, platform or the like 13, a first translating arm 14 carried by the base 13 on one side thereof, a second translating arm 16 carried by the base 13 on another side thereof, wherein the sides are in the cephalad/caudal direction when the spinal retractor 10 is used, and a middle arm 18 carried by the base between the first and second translating arms 14, 16, wherein the middle arm is in the lateral/medial direction when the spinal retractor 10 is used. The base 13 further has a first side arm or wing 24 extending from a first side of the base 13 and a second side arm or wing 26 extending from a second side of the base 13. The first and second side arms 24, 26 extend generally in opposite directions relative to each other but with a slight inward angle as shown. The first and second side arms 24, 26 are in the cephalad/caudal direction when the spinal retractor 10 is used.

The spinal retractor 10 is designed to be fixed relative to a surgical site particularly, but not necessarily, to an external frame or the like (not shown) that is fixed relative to the patient. The spinal retractor 10 is also configured for rotation relative to the external frame. As such the base 13 has a boss 22 situated between opposite edges 25, 27, the boss 22 defining a face 23 from which projects a post, shaft, pole, bar, rod, stick or the like (i.e. a projection) 21. The spinal retractor 10 is connected with the external frame via the projection 21 which is received in or by a clamp, holder, receiver or the like (not shown) of the external frame. The projection 21 has a textured or keyed outer surface for engagement with the external frame, shown in the figures as radially spaced longitudinal grooves. The external surface of the projection 21 aids in positive engagement of the spinal retractor 10 with the external frame in order to fix rotational position of the spinal retractor 10 relative to the external frame.

A housing 28 is disposed on the base 13 between the first and second side arms 24, 26 and has an opening that receives the arm 18. The housing 28 cooperates with the arm 18 to provide adjustment of the arm 18 relative to the housing 28. Particularly, the arm 18 has a plurality of teeth, serrations or the like 51 on an inside edge thereof while the housing 28 includes ratchet components that cooperate with the teeth 51 of the arm 18 to provide ratcheting adjustability/translation of the arm 18 relative to the base 13. A button 29 is associated with the housing 28 and is coupled to the internal ratchet components thereof in order to allow release of the ratcheted (fixed) position of the arm 18 relative to the housing 28. In this manner, the arm 18 translates or slides in and out relative to the housing 28/base 13. Additionally, since a blade assembly 48, as described more fully below, is connected to the arm 18, the blade assembly 48 translates relative to the housing 28/base 13. This allows the blade assembly 48 to be positioned relative to the housing 28/base 13 and to the other blade assemblies 50, 52. Because of its position, the arm 18 and thus the blade assembly 48 translate or move in the medial/lateral directions when the spinal retractor 10 is in use. Position of the blade assembly 48 affects and effects retraction of tissue at the surgical site, particularly in the medial/lateral directions.

A housing 30 is disposed on an end of the first side arm 24 and has an opening that receives the first translating arm 14. The housing 30 cooperates with the first translating arm 14 to provide adjustment of the first translating arm 14 relative to the housing 30. Particularly, the first translating arm 14 has a plurality of teeth, serrations or the like 41 on an inside edge of an end 39 of the first translating arm 14 while the housing 30 includes ratchet components that cooperate with the teeth 41 of the first translating arm 14 to provide ratcheting adjustability/translation of the first translating arm 14 relative to the first side arm 24/base 13. A button 31 is associated with the housing 30 and is coupled to the internal ratchet components thereof in order to allow release of the ratcheted (fixed) position of the first translating arm 14 relative to the housing 30. In this manner, the first translating arm 14 translates or slides in and out relative to the housing 30/first side arm 24. Additionally, since the blade assembly 50, as described more fully below, is connected to the first translating arm 14, the blade assembly 50 translates relative to the housing 30/first side arm 24. This allows the blade assembly 50 to be positioned relative to the housing 30/first side arm 24 and to the other blade assemblies 48, 52.

Mention is now made to the configuration of the first translating arm 14. The first translating arm 14 is angled or bent so as to define a "boomerang" shape—i.e. an elbow or bend 38 between arm segments 36 and 39. Particularly, arm segments 36, 39 are bent to have an internal angle of less than ninety degrees (angle<90°) with around seventy degrees (70°) being shown and preferred. Other angles, of course, may be used. A head 37 is provided at an end of the arm segment 36 opposite the bend 38 and is angled so as to project essentially parallel with the arm segment 39. The head 37 holds the blade assembly 50. As seen, the first translating arm 14 is angled so that its blade assembly 50 is proximate the blade assembly 48 of the arm 18.

The first translating arm 14 moves in and out relative to the housing 30 and thus the first side arm 24 through ratcheting of the arm segment 39 with its plurality of teeth 41 cooperating with the ratchet components of the housing 30. Movement of the arm 14 moves the corresponding blade assembly 50 relative to the other blade assemblies 48, 52. Because of its position and connection with the housing 30, the first translating arm 14 translates or moves in the cephalad/caudal directions so that the blade assembly 50 also moves in the cephalad/caudal directions. Position of the blade assembly 50 affects and effects retraction of tissue at the surgical site, particularly in the cephalad/caudal directions.

A housing 32 is disposed on an end of the second side arm 26 and has an opening that receives the second translating arm 16. The housing 32 cooperates with the second translating arm 16 to provide adjustment of the second translating arm 16 relative to the housing 32. Particularly, the second translating arm 16 has a plurality of teeth, serrations or the like 47 on an inside edge of an end 45 of the second translating arm 16 while the housing 32 includes ratchet components that cooperate with the teeth 47 of the second translating arm 16 to provide ratcheting adjustability/translation of the second translating arm 16 relative to the second side arm 26/base 13. A button 32 is associated with the housing 32 and is coupled to the internal ratchet components thereof in order to allow release of the ratcheted (fixed) position of the second translating arm 16 relative to the housing 32. In this manner, the second translating arm 16 translates or slides in and out relative to the housing 32/second side arm 26. Additionally, since the blade assembly 52, as described more fully below, is connected to the second translating arm 16, the blade assembly 52 translates relative to the housing 32/second side arm 26. This allows the blade assembly 52 to be positioned relative to the housing 32/second side arm 26 and to the other blade assemblies 48, 50.

Mention is now made to the configuration of the second translating arm 16. The second translating arm 16 is angled or bent so as to define a "boomerang" shape—i.e. an elbow or bend 44 between arm segments 42 and 45. Particularly, arm segments 42, 45 are bent to have an internal angle of less than ninety degrees (angle<90°) with around seventy degrees (70°) being shown and preferred. Other angles, of course, may be used. A head 43 is provided at an end of the arm segment 42 opposite the bend 44 and is angled so as to project essentially parallel with the arm segment 45. The head 43 holds the blade assembly 52. As seen, the second translating arm 16 is angled so that its blade assembly 52 is proximate the blade assembly 48 of the arm 18.

The second translating arm 16 moves in and out relative to the housing 32 and thus the second side arm 26 through ratcheting of the arm segment 45 with its plurality of teeth 47 cooperating with the ratchet components of the housing 32. Movement of the arm 16 moves the corresponding blade assembly 52 relative to the other blade assemblies 48, 50. Because of its position and connection with the housing 32, the second translating arm 16 translates or moves in the cephalad/caudal directions so that the blade assembly 52 also moves in the cephalad/caudal directions. Position of the blade assembly 52 affects and effects retraction of tissue at the surgical site, particularly in the cephalad/caudal directions.

Ratcheting adjustment of the arm 18 and of the first and second translating arms 14, 16 (and thus adjustment of the blade assemblies 48, 50, 52) may be accomplished manually but are preferably adjusted via one or more surgical instruments or tools. As such, the arms 18, 24, 26 and the base 13 are configured to allow manipulation of the arms 18, 24, 26 by a surgical instrument or tool (not shown).

Figure 4:
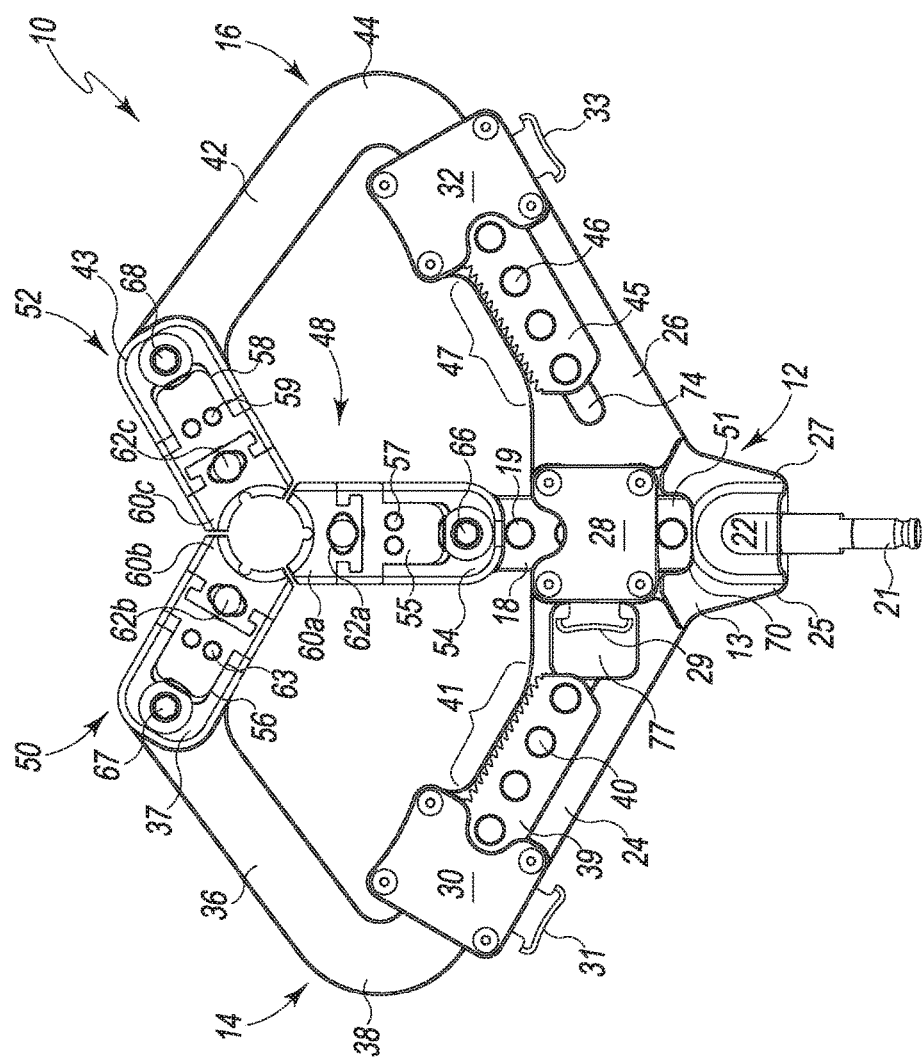
FIG. 4 is a top plan view of the spinal retractor of FIG. 1 in a closed position.

As best seen in FIGS. 1 and 4, the arm 18 has a series of holes 19 that extend along its longitudinal length. The base 13 has a slot 70 that extends through the housing 28 and which is sized to receive the arm 18. The arm 18 thus translates within the slot 70. One or more holes 19 of the arm 18 accepts a surgical instrument, tool and/or instrument/tool portion to manually move the arm 18 within the slot 70 and in conjunction/cooperation with the ratcheting housing 28. As should be appreciated, the ratcheting housing 28 allows incremental locking movement of the arm 18 in one direction while prohibiting movement in an opposite direction without the release thereof. In the case of arm 18, the arm 18 incrementally locks in a direction toward the base 13 in order to hold tissue by the blade assembly 48 in the medial/lateral direction. This allows the surgeon to incrementally manipulate the blade assembly 48 and thus the amount of tissue retraction by the blade assembly 48. Release is accomplished by the button/ratchet release system 29 associated with the housing/ratchet system 28. As best seen in FIG. 4, the button 29 extends from the housing 28 into a configured notch or recess 77 in the first side arm 24. Recessing the button 29 helps to prevent accidental activation and thus release of tissue retraction.

Figure 3:
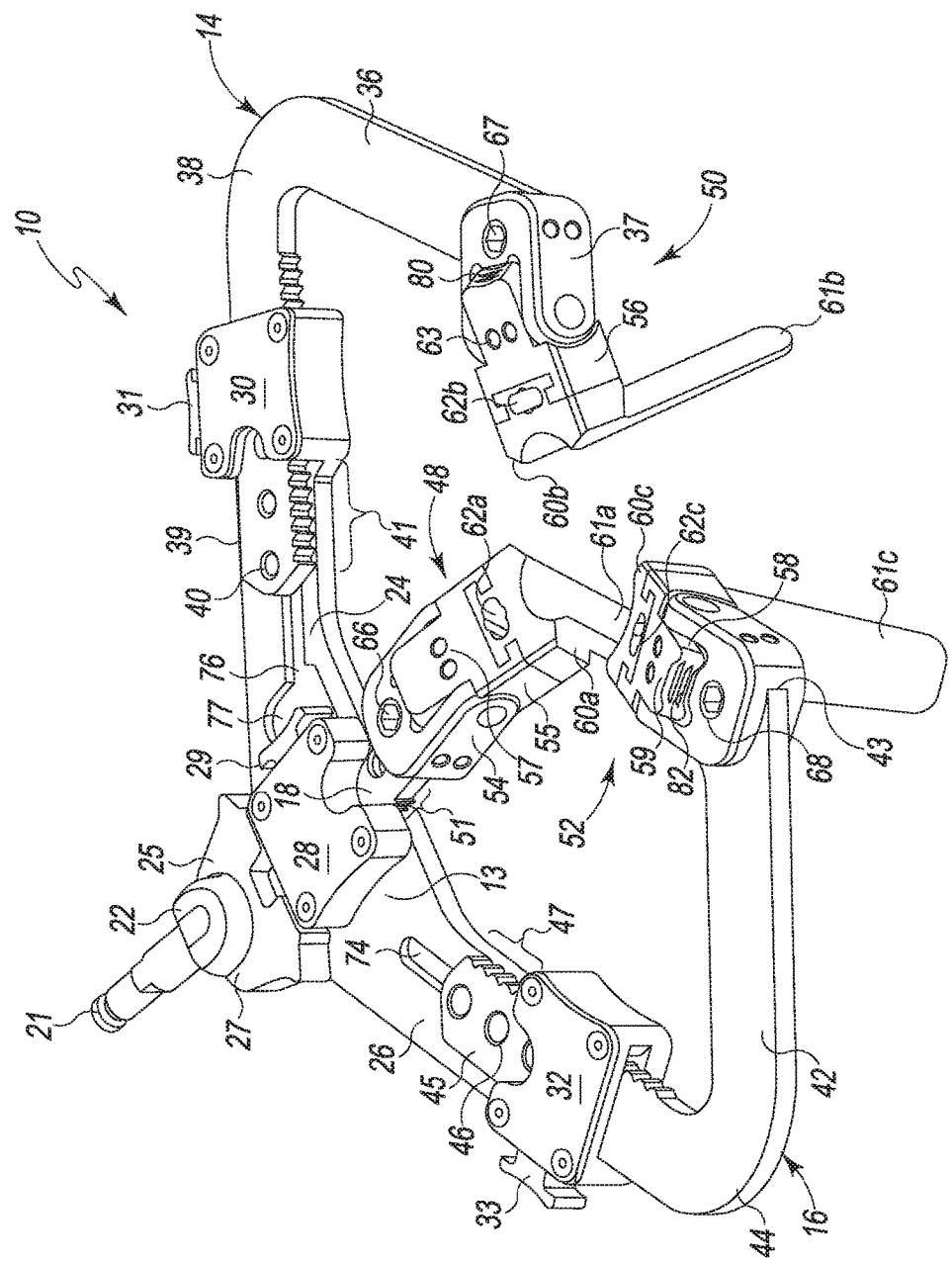
FIG. 3 is another topside view of the spinal retractor of FIG. 1 in an open position.

As best seen in FIGS. 1, 3 and 4, the first translating arm 14 has a series of holes 40 that extend along a length of the end segment 39. In conjunction therewith, the first side arm 24 of the base 13 has a slot 76 that extends from the configured recess 77 into the housing 30. The slot 76 is sized both in width and length to fit under the arm segment 39 and particularly under the holes 40. One or more holes 40 of the first translating arm 14 accepts a surgical instrument, tool and/or instrument/tool portion to manually move the arm 14 over the slot 76 and in conjunction/cooperation with the ratcheting housing 30. As should be appreciated, the ratcheting housing 30 allows incremental locking movement of the arm 14 in one direction while prohibiting movement in an opposite direction without the release thereof. In the case of the first translating arm 14, the arm 14 incrementally locks in a direction along the longitudinal length of the first side arm 24 inwardly toward the base 13 in order to hold tissue by the blade assembly 50 in the cephalad/caudal direction. This allows the surgeon to incrementally manipulate the blade assembly 50 and thus the amount of tissue retraction by the blade assembly 50. Release is accomplished by the button/ratchet release system 31 associated with the housing/ratchet system 30. The button 31 extends outward from the housing 30 helping to prevent accidental activation and thus release of tissue retraction.

As best seen in FIGS. 1, 3 and 4, the second translating arm 16 has a series of holes 46 that extend along a length of the end segment 45. In conjunction therewith, the second side arm 26 of the base 13 has a slot 74 that extends from proximate an end of the second side arm 26 near the base 13 and into the housing 32. The slot 74 is sized both in width and length to fit under the arm segment 45 and particularly under the holes 46. One or more holes 46 of the second translating arm 16 accepts a surgical instrument, tool and/or instrument/tool portion to manually move the arm 16 over the slot 74 and in conjunction/cooperation with the ratcheting housing 32. As should be appreciated, the ratcheting housing 32 allows incremental locking movement of the arm 16 in one direction while prohibiting movement in an opposite direction without the release thereof. In the case of the second translating arm 16, the arm 16 incrementally locks in a direction along the longitudinal length of the second side arm 26 inwardly toward the base 13 in order to hold tissue by the blade assembly 52 in the cephalad/caudal direction. This allows the surgeon to incrementally manipulate the blade assembly 52 and thus the amount of tissue retraction by the blade assembly 52. Release is accomplished by the button/ratchet release system 33 associated with the housing/ratchet system 32. The button 33 extends outward from the housing 32 helping to prevent accidental activation and thus release of tissue retraction.

Figure 2:
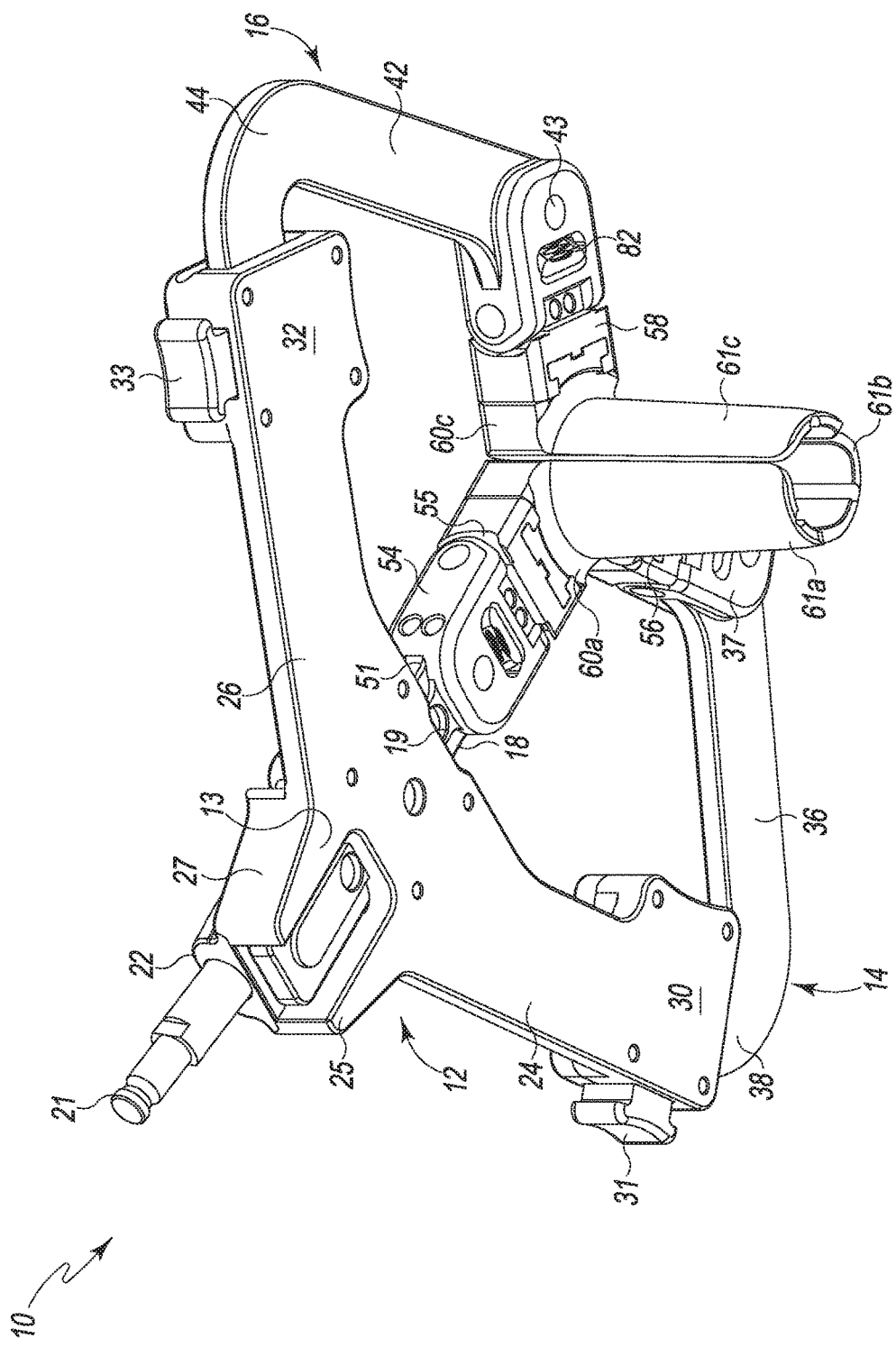
FIG. 2 is an underside view of the spinal retractor of FIG. 1 shown in a closed position.

As seen in the figures each arm 18, 14 and 16 has a respective blade assembly 48, 50, 52 for holding and retracting tissue during spinal surgery. The blade assembly 48 includes a head 54 which pivotally retains a blade holder 57 via an angulation system controlled by a set screw 66, the head 54 holding a blade 60a. The blade assembly 50 includes the head 37 which pivotally retains a blade holder 56 via an angulation system controlled by a set screw 67, the head 37 holding a blade 60b. The blade assembly 52 includes the head 43 which pivotally retains a blade holder 58 via an angulation system controlled by a set screw 68, the head 43 holding a blade 60c. The blades 60a, 60b and 60c are preferably, and as shown, identical. While each blade assembly 48, 50, 52 is identical, one or more blade assembly may be different as desired. However, in the preferred embodiment as shown, the three blade assemblies forming a triangular blade assemblage, are identical and fashioned in accordance with the present principles. Therefore, description of one blade assembly of the blade assemblies 48, 50, 52 describes the others of the blade assemblies 48, 50, 52. Moreover, the description of one blade 60a, 60b, 60c of the blade assemblies 48, 50, 52 describes the others of the blades 60a, 60b, 60c. In general, the blade assemblies 48, 50, 52 are each designed for up/down or posterior/anterior translation or angulation. In FIGS. 1, 2 and 4, the blade assemblies 48, 50, 52 are in a 0° or non-angulated position as well as in an un-retracted position. In FIG. 3, the blade assemblies 48, 50, 52 are in a downwardly angled position (an angle downwardly from 0°) as well as in a retracted position.

Figure 5:
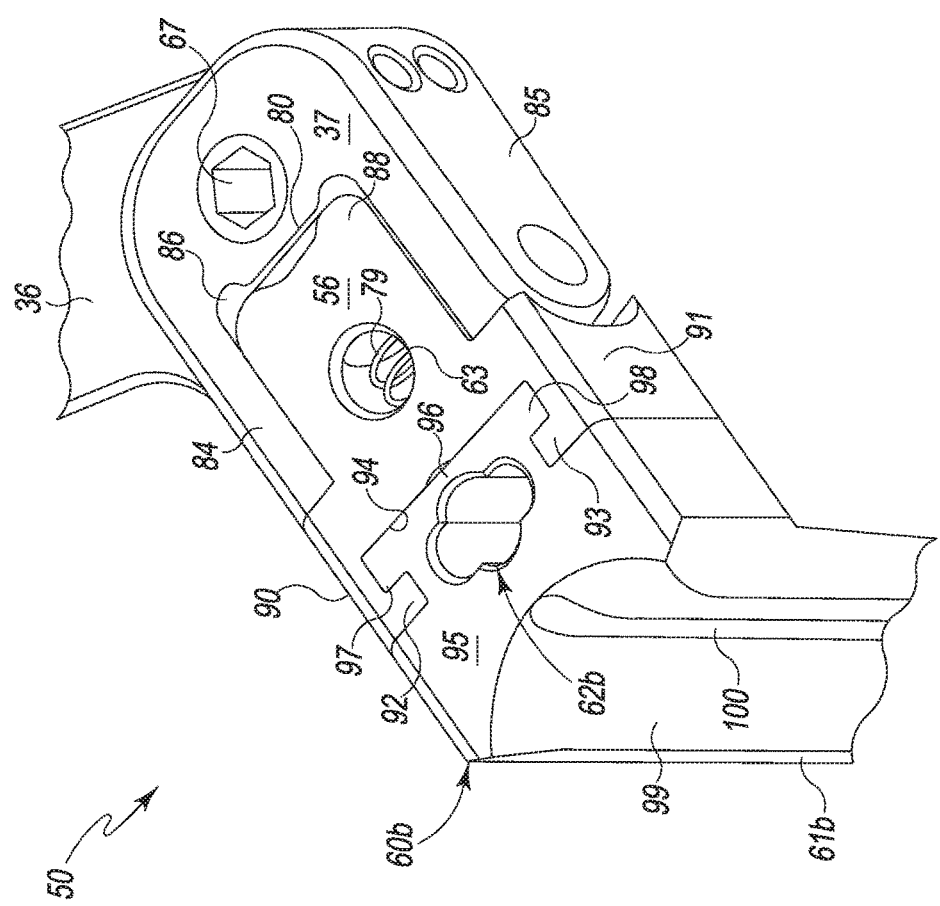
FIG. 5 is an enlarged topside view of a blade assembly on an arm of the spinal retractor of FIG. 1.

With particular reference to FIG. 5 the details of a blade assembly and blade will be described with reference to blade assembly 50. As seen, the blade holder 56 is shown in a 0° position wherein the blade 60b is in a full upright or vertical position. The blade holder 56 is pivotally coupled to the head 37. Particularly, an end or tongue 88 of the blade holder 56 is received within a cutout 86 of the head 37 and pivotally connected at sides thereof to arms 84 and 85 of the head 37. This allows the blade holder 56 to pivot relative to the head 37. The blade holder 56 and the head 37 are connected via the angulation adjustment system 63 which includes a worm gear system driven by the hex nut 67. Particularly (and in conjunction with FIG. 3) the hex nut 67 is externally threaded to mesh with screw serrations 80 on an end of the blade holder 56. As the hex nut 67 is rotated clockwise or counterclockwise the blade holder 56 will angulate or pivot up and down. As the blade holder 56 angulates or pivots downward, the spade portion 61b of the blade 60b moves outwardly (medially or laterally) to effect splaying of the tissue. As seen in FIG. 3, the blade holder 58 includes screw serrations 82 on an end thereof as part of its angulation adjustment system 59.

The blade holder 56 has first and second side arms 90, 91 that define a configured notch 94 that is adapted to receive a configured flange 96 of a head 95 of the blade 60b. The blade holder 56 and the blade 60b are configured to allow the blade 60b to be positively received and held, removed and replaced. Inwardly projecting ends 92, 93 of the first and second side arms 90, 91 define a confined slot for receipt and retention of the blade head 96, the blade flange 96 having lips 97, 98 for complementary reception by the ends 92, 93. The blade 60b is thus vertically inserted into and removed from the blade holder 56.

The blade holder 56 incorporates a spring loaded detent system 79 which releasably locks the blade 60b into the blade holder 56. The blade 60b has a keyed access point 62b to allow both insertion of the blade 60b into the blade holder 56 as well as actuation of the detent system 79 in order to release the blade 60b from the blade holder 56.

The blade 60b has a tong, spade, paddle or the like 61b that extends transverse from the head 95. An inner surface 99 of the paddle 61b is curved inwardly (i.e. concave relative to the head 95). A channel 100 extends from a top of the paddle 61b (i.e. the top of the concavity 99) to an end of the paddle 61b. The channel 100 receives a shaft that permits anatomical docking of the blade to bony anatomy and/or a cannula in which lighting may be inserted to aid in intraoperative visualization. Rounded corners permit the finestra formed by the blades 60a, 60b, 60c to maintain the same diameter as the blades are angulated.

It should be appreciated that the present spinal retractor 10 provides a table mount connection to secure retractor position relative to the patient via the frame (table). The cephalad/caudal translating arms incrementally lock positions via ratcheting teeth within each ratchet housing and subsequently expand both soft tissue retraction by means of the blades. Each translating arm can be moved independently. The cephalad/caudal translating arms cooperate and co-act with the medial/lateral translating arm to provide a stable finestra and retraction. Thumb actuated depressors release the locked positions of the arms and thus the blades. Adjustable convergence of each translating arm 14, 16, 18 with respective blades creates an adjustable finestra to the surgical site.

Referring now to FIGS. 6-21C, a spinal retractor assembly 210 is shown according to one embodiment. As discussed in greater detail below, retractor assembly 210 may share various functional and structural features with spinal retractor 10. In one embodiment, retractor assembly 210 includes a frame or base 212 (e.g., a plate, frame, or base assembly, etc.), a first side assembly 214, a second side assembly 216, and a center assembly 218. Assemblies 214, 216, and 218 are coupled to base 212 to enable translating movement of assemblies 214, 216, 218 relative to base 212 to provide retraction of tissue, etc. during surgical procedures involving the spine, etc. First and second side assemblies 214, 216 translate relative to frame 212 in a medial-lateral direction (e.g., along a first axis or direction), and center assembly 218 translates relative to frame 212 in a cephalad-caudal direction (e.g., along a second axis or direction) in a generally perpendicular fashion relative to first and second assemblies 214, 216. In one embodiment, each of assemblies 214, 216, 218 may be adjusted (e.g., translated) relative to frame 212 independently (e.g., such that each of assembly 214, assembly 216, and assembly 218 may be adjusted individually).

Figure 6:
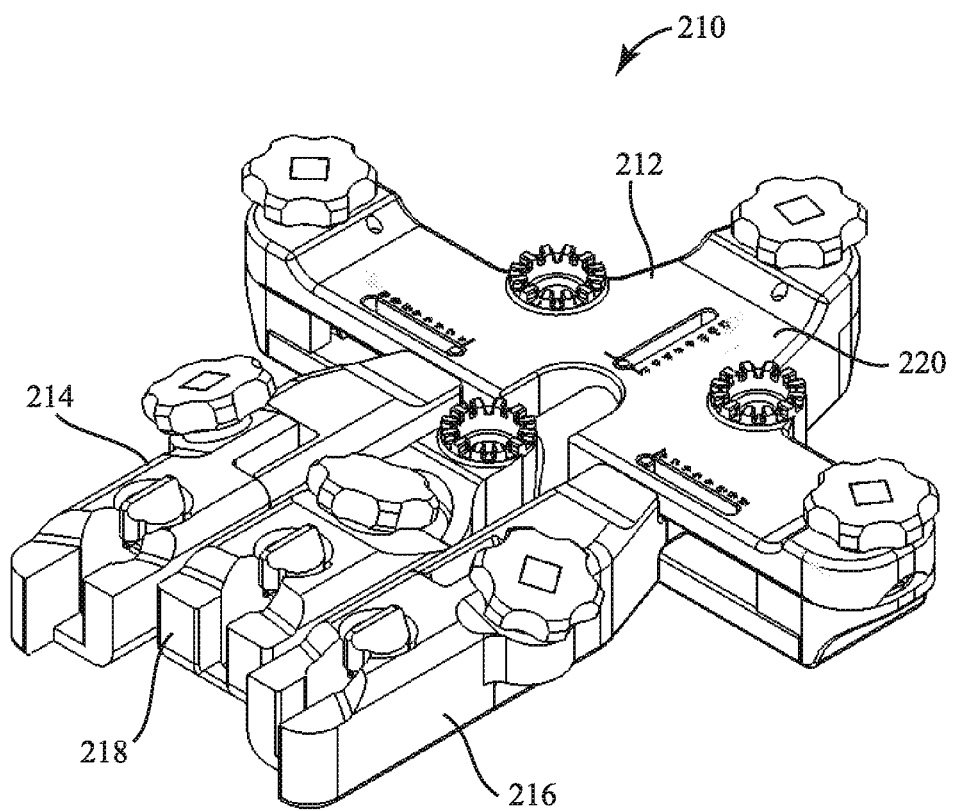
FIG. 6 is a perspective view of a spinal retractor according to an alternative embodiment.
Figure 10:
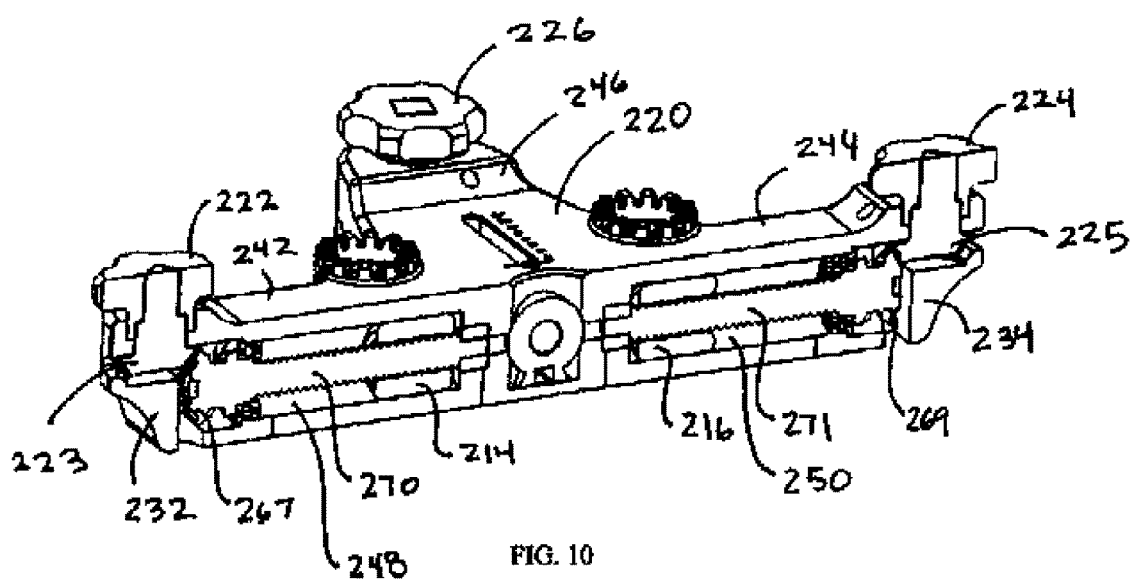
FIG. 10 is a cross-sectional perspective view taken along line 10-10 of FIG. 7 according to one embodiment.

Referring to FIGS. 6 and 10, frame 212 includes body 220, a first side adjustment member or knob 222, a second side adjustment member or knob 224, and a center adjustment member or knob 226. Knobs 222, 224 are coupled to drive members 223, 225, respectively, such that rotation of knobs 222, 224, causes a corresponding rotation of drive members 223, 225. Drive members 223, 225 include bevel gears in one embodiment and, as discussed in greater detail below, are configured to engage bevel gears on corresponding adjustment members. Knob 226 may be coupled to a drive member of similar structure and function.

Figure 7:
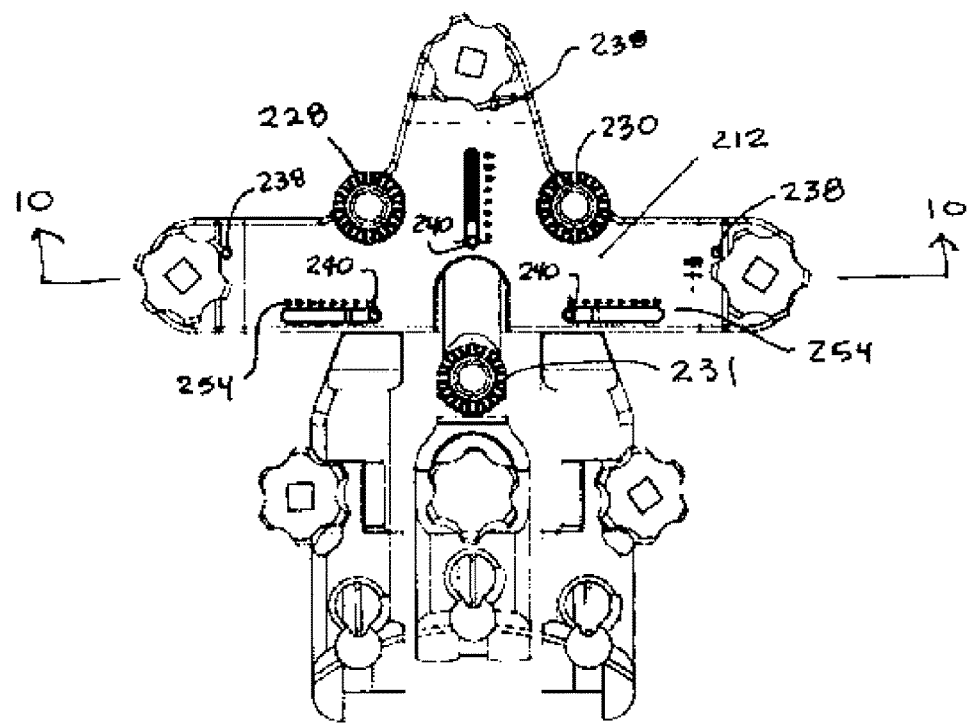
FIG. 7 is a top view of the spinal retractor assembly of FIG. 6 according to one embodiment.
Figure 8:
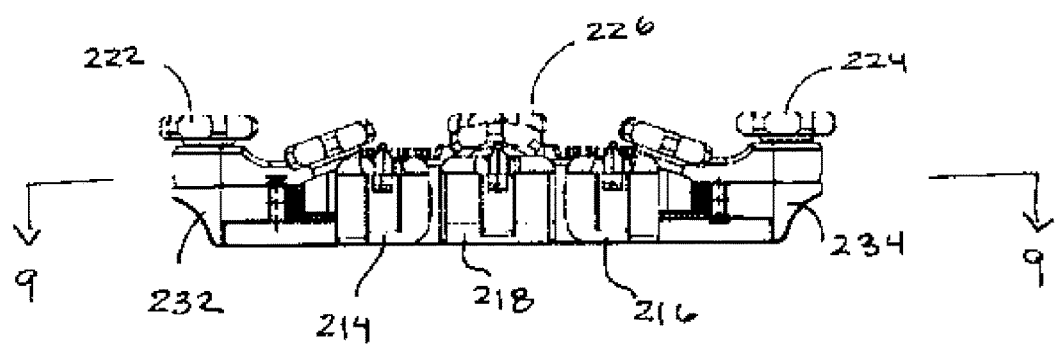
FIG. 8 is a front view of the spinal retractor assembly of FIG. 6 according to one embodiment.

In one embodiment, frame 212 further includes table arm mounts 228, 230, 231 (see FIG. 7). Mounts 228, 230, 231 are configured to enable attachment of retractor assembly 210 to a table arm in a fixed relationship. As such, retractor assembly 210 may be fixed in space via one or both of table mounts 228, 230, 231. Mounts 228, 230, 231 may be located in any suitable locations, and more or fewer mounts may be provided than illustrated according to various alternative embodiments.

Figure 9:
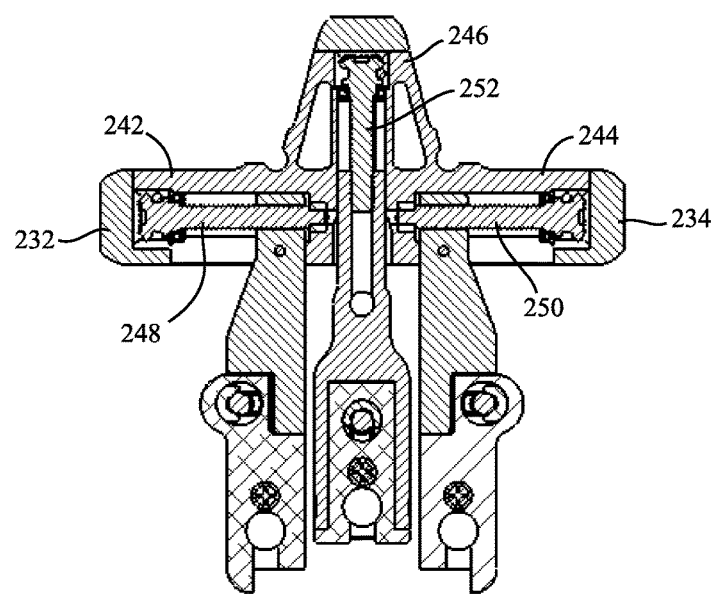
FIG. 9 is a cross-sectional view taken along line 9-9 of FIG. 8 according to one embodiment.
Figure 14:
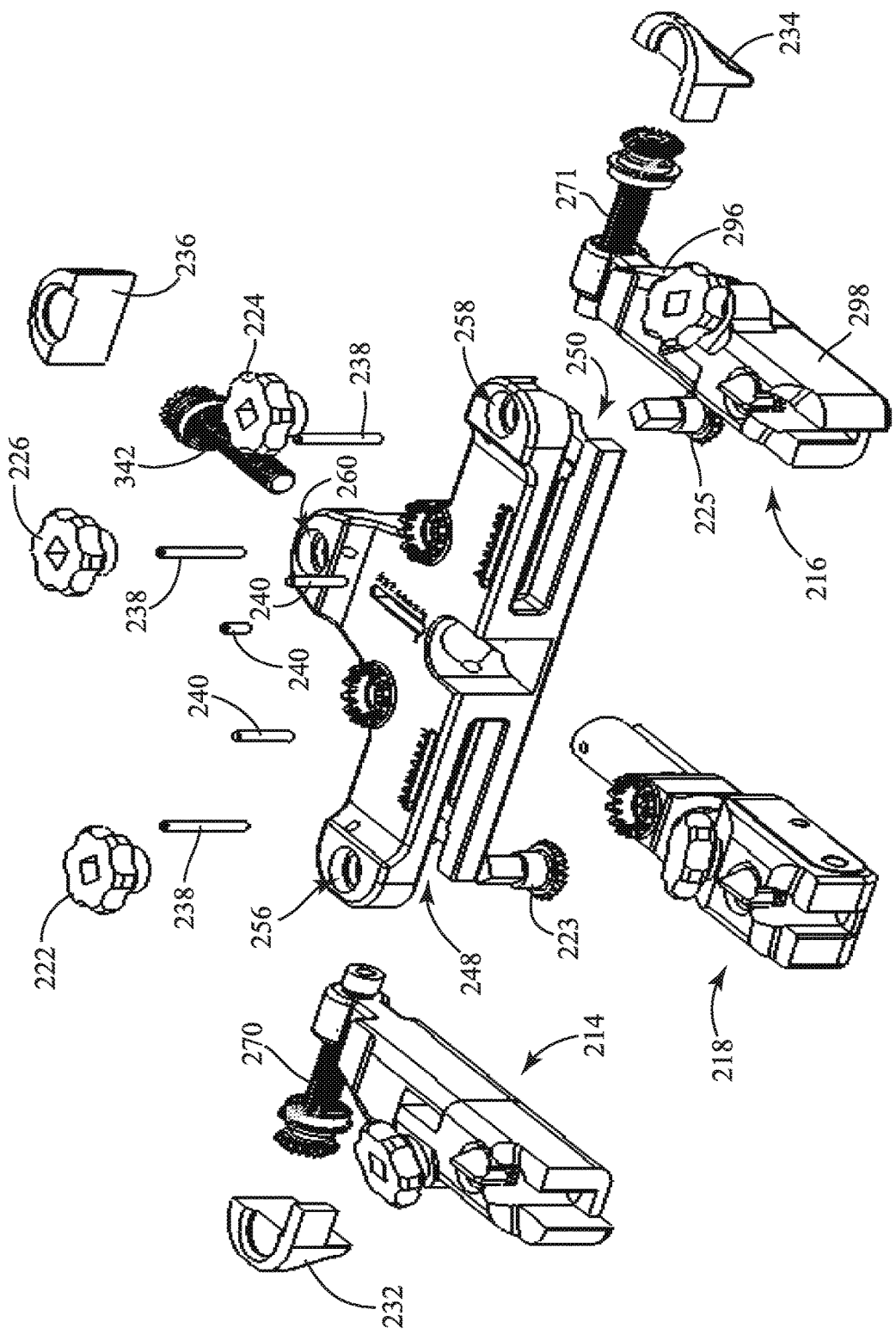
FIG. 14 is an exploded view of the spinal retractor of FIG. 6 according to one embodiment.

Referring FIGS. 9-10 and 14, in some embodiments frame 212 includes first and second side retainers 232, 234. Side retainers are positioned at the lateral ends of frame 212 and form at least a portion of the channels within which assemblies 214, 216 translate. In one embodiment, retainers 232, 234 define a limit to the range of motion of first and second side assemblies 214, 216. Retainers 232, 234 may be coupled to body 220 using any suitable fastening technique, including welding, press fits, mechanical fasteners, and the like. As shown in FIG. 14, a center retainer 236 similarly is coupled to a center portion of body 220 using any suitable fastening technique, including welding, press fits, mechanical fasteners, and the like.

In some embodiments, retaining pins 238 extend through body 220 and, as discussed in greater detail below, are received within annular grooves in threaded members to hold the threaded members in position during use of retractor assembly 210. In one embodiment, three retaining pins 238 are utilized. In other embodiments, more or fewer retaining pins may be used. Further, marker pins 240 may be used in connection with each of first side assembly 214, second side assembly 216, and center assembly 218. Marker pins 240 extend up from assemblies 214, 216, and 218 and through body 220 to provide an indication of the positions of assemblies 214, 216, and 218 relative to body 220, thereby providing a user of retractor assembly 210 a visual indication of the amount of retraction being provided by each of assemblies 214, 216, and 218. In one embodiment, body 220 includes marking gauges 254 (see FIG. 7) having incremental distance markings to provide further information regarding amounts of retraction. Thus, the amount of retraction is indicated by the position of the marking pins 240 along marking gauges 254.

In one embodiment, body 220 includes a first lateral extension 242, a second lateral extension 244, and a central extension 246 (see FIG. 9). First and second lateral extensions 242, 244 generally extend along a common first axis, and central extension 246 generally extends along a second axis perpendicular to the first axis. Central extension 246 is in one embodiment positioned at approximately the midpoint between the opposite ends of first and second lateral extensions 242, 244. A first lateral channel 248 is formed in first lateral extension 242, a second lateral channel 250 is formed in second lateral extension 244, and a central channel or bore 252 is formed in central extension 246. Channels 248, 250, 252 receive end portions of first side assembly 214, second side assembly 216, and center assembly 218, respectively. A first side adjustment aperture 256 is provided on first lateral extension 242, a second side adjustment aperture 258 is provided in second lateral extension 244, and a center adjustment aperture 260 is provided in center extension 246. Adjustment apertures 256, 258, 260 are configured to receive adjustment knobs and/or drive members to enable user-adjustment of first side assembly 214, second side assembly 216, and center assembly 218 relative to body 220.

Referring to FIG. 10, translation of first and second side assemblies 214, 216 is accomplished via rotation of adjustment knobs 222, 224. Adjustment knobs 222, 224 are coupled to drive members 223, 225, which may include bevel gears. Drive members 223, 225 in turn engage bevel gears 267, 269 provided on opposing ends of threaded adjustment members 270, 271, such that rotation of knobs 222, 224 causes a corresponding rotation of adjustment members 270, 271. First and second side assemblies 214, 216 are threadingly received by adjustment members 270, 271 such that rotation of adjustment members 270, 271 causes translation of first and second side assemblies 214, 216. Central assembly is movable in a similar fashion, through use of adjustment knob 226 and adjustment member 342. As such, through selective rotation of knobs 222, 224, and 226, first and second side assemblies 214, 216 and central assembly 218 may be translated independently from one another relative to body or frame 212.

Figure 11:
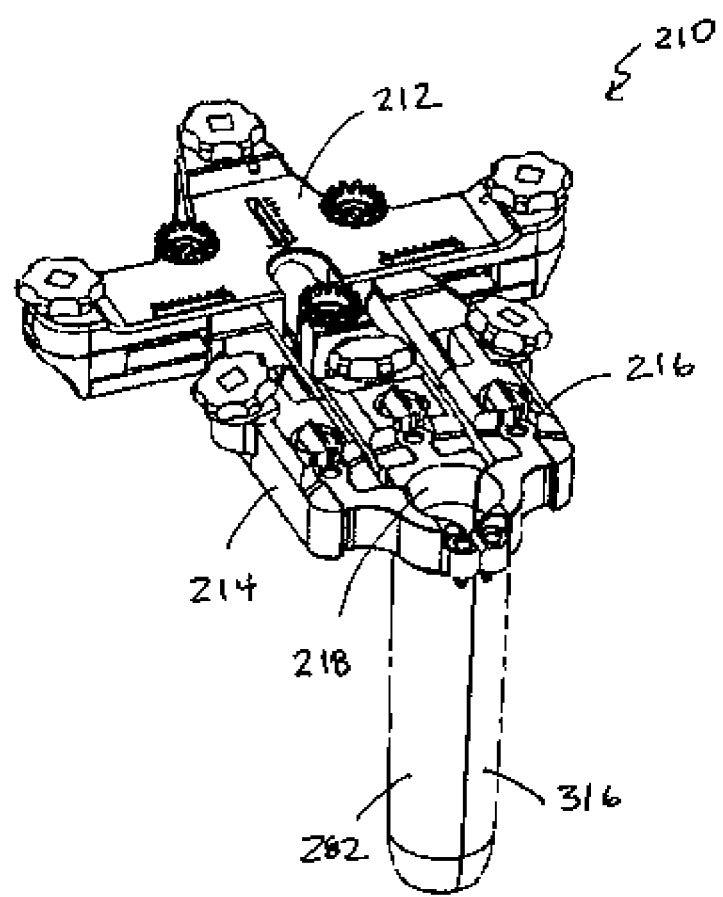
FIG. 11 is a perspective view of a spinal retractor in a closed configuration according to one embodiment.
Figure 12:
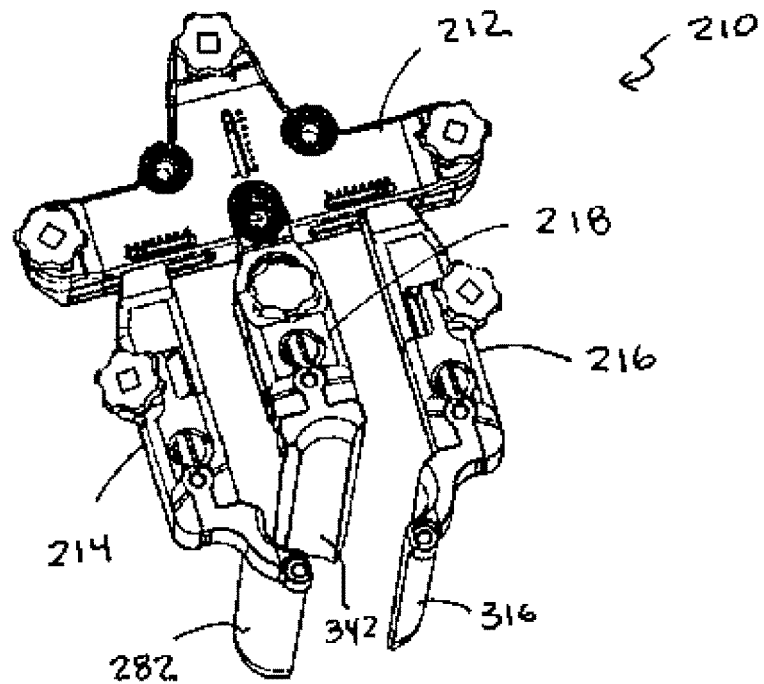
FIG. 12 is a perspective view of the spinal retractor of FIG. 11 in an open configuration according to one embodiment.
Figure 13:
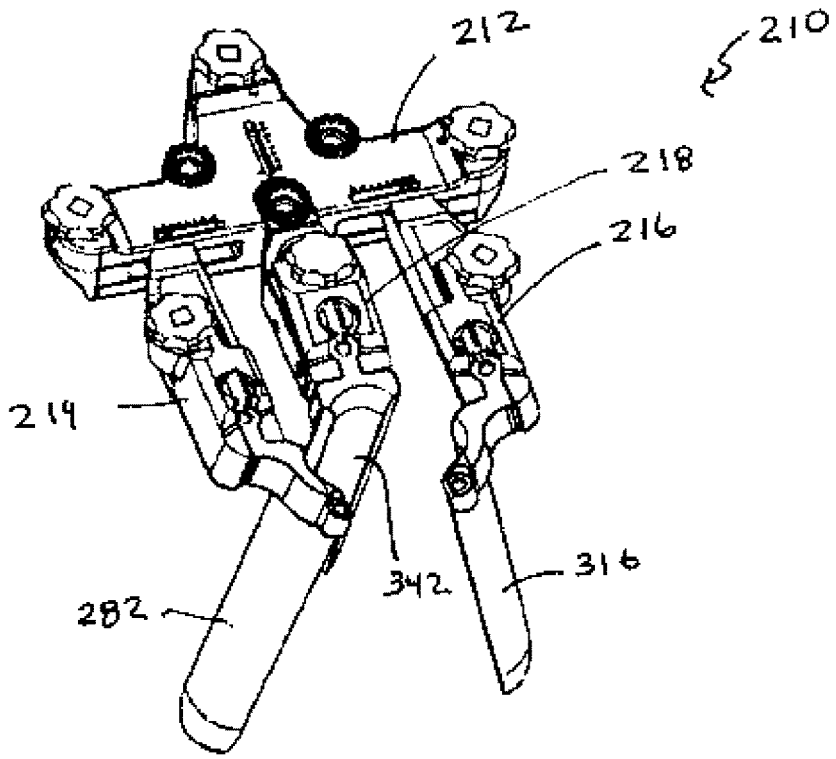
FIG. 13 is a perspective view of the spinal retractor of FIG. 11 in an open configuration with angulated blades according to one embodiment.

Referring to FIGS. 11-13, assembly 210 is movable between a closed configuration, shown in FIG. 11, to an open configuration, shown in FIG. 12, through translation of first and second side assemblies 214, 216 and/or central assembly 218 relative to body 220. Furthermore, first and second side assemblies 214, 216 and central assembly 218 receive blade assemblies 282, 316, and 348, respectively, which are configured to hold tissue apart during various procedures. As shown in FIGS. 12 and 14 and as discussed in greater detail below, blade assemblies 282, 316, 342 may be angulated (e.g., moved from a generally vertical orientation to one or more non-vertical, or angled, orientations) to suit a particular procedure.

Figure 15A:
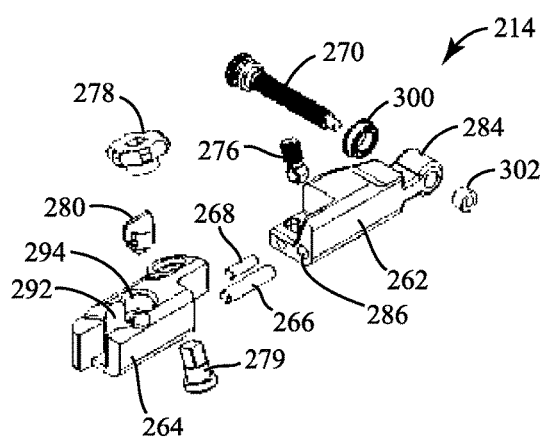
FIGS. 15A-15B illustrate a side assembly of a spinal retractor according to one embodiment.
Figure 15B:
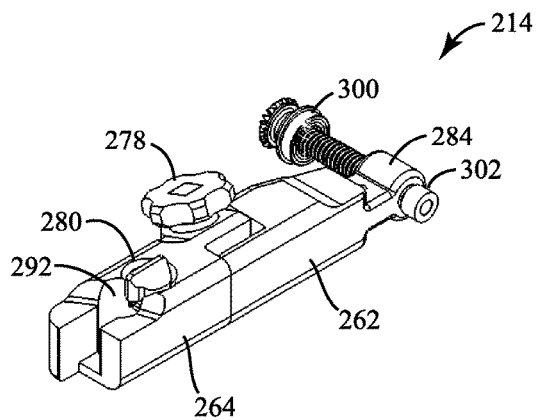

Referring now to FIGS. 15A-15B, first side assembly 214 is shown in greater detail according to one embodiment. Assembly 214 includes a first arm portion 262 coupled to a second arm portion 264. First arm portion 262 and second arm portion 264 can take any suitable size and/or shape, and be coupled together using a variety of coupling methods.

In one embodiment, first arm portion 262 is translatable relative to frame 212, but rotatably fixed relative to frame 212, and second arm portion 264 is rotatably coupled to first arm portion 262. As shown in FIGS. 18A-19B, second arm portion rotates relative to first arm portion 262 about a first pivot pin 266. An adjustment knob 278 is coupled to an insert 279 which threadingly engages an angulation adjustment member 276. Member 276 includes a threaded shaft and rotates about a second pivot pin 268. As shown in FIGS. 18A-19B, as a user turns knob 278, the angular position of second arm portion 264 relative to first arm portion 262 changes due to the travel of insert 279 along member 276, providing angular adjustability of the associated blade assemblies. For example, as shown in FIGS. 18A-B, first and second arm portions 262, 264 are generally aligned, and knob 278 is in a first position. Upon turning knob 278, knob 278 moves to a second position, shown in FIGS. 19A-B, and second arm portion 264 moves to an angulated position with respect to first arm portion 262, thereby enabling additional retraction of surrounding tissue, etc.

Referring to FIG. 15A, first arm portion 262 includes an internally threaded cylindrical portion 284. Portion 284 is received within channel 248 and translates therein. In some embodiments, the outer contour of portion 284 generally corresponds in shape to the inner contour of channel 248 such that portion 284 is limited to translational movement within channel 248. In one embodiment, portion 284 is received within bushings 300, 302, which are provided on threaded member 270 and may act to enable rotation of threaded member 270 within channel 248 and/or define the range of motion of portion 284. First arm portion 262 further includes pin apertures 286, which are sized and shaped to receive first and second pivot pins 266, 268. In order to provide the angulation of second arm portion 264, first arm portion 262 further includes an adjustment surface 288. As shown in FIGS. 18A and 19A, adjustment surface 288 in one embodiment limits the total amount of angulation of second arm portion 264 relative to first arm portion 262.

Second arm portion 264 includes a blade receiving portion 292 and a blade lock bore 294. Blade receiving portion 292 is configured to receive first side blade assembly 282, and blade lock bore 294 is configured to receive blade lock 280. In one embodiment, blade lock 280 includes a non-circular head such that blade lock 280 is rotatable within blade lock bore 294 into and out of an interfering position relative to first side blade assembly 282 when first side blade assembly 282 is received within blade receiving portion 292. As such, first side blade assembly 282 may be slidingly received within blade receiving portion 292 and subsequently maintained in position relative to second arm portion 264 by way of blade lock 280.

Second side assembly 216 in one embodiment operates in a similar manner to first side assembly 214, and includes similar components, including a first arm portion 296 and a second arm portion 298, which receives second blade assembly 316.

Figure 16A:
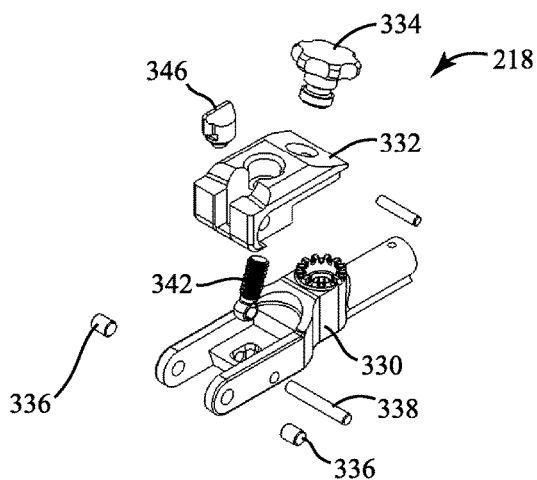
FIGS. 16A-16B illustrate a central assembly of a spinal retractor according to one embodiment.
Figure 16B:
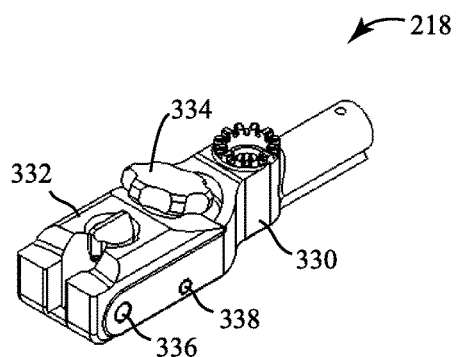

Referring to FIGS. 16A-16B, center assembly 218 includes a first arm portion 330 and second arm portion 332 pivotally coupled to first arm portion 330 via pivot pins 336. An angulation knob 334 threadingly engages an adjustment member 342 to cause rotation of adjustment member 342 about angulation pivot pin 338. Center blade assembly 342 is received by second arm portion 332 and retained in place by a blade lock 346. Rotation of adjustment knob 344 causes a corresponding change in the angulation of center blade assembly 342.

Figure 17:
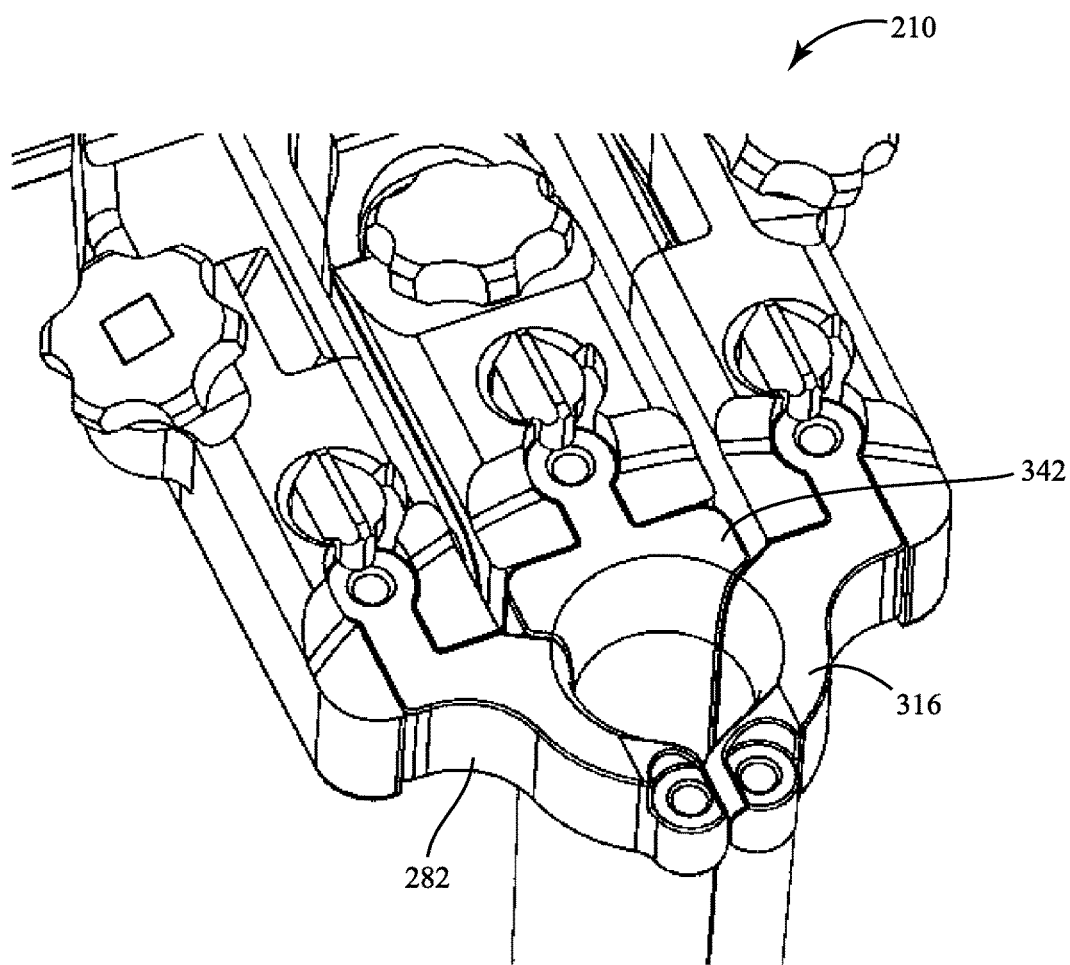
FIG. 17 is a perspective view of a portion of a spinal retractor according to one embodiment.
Figure 20A:
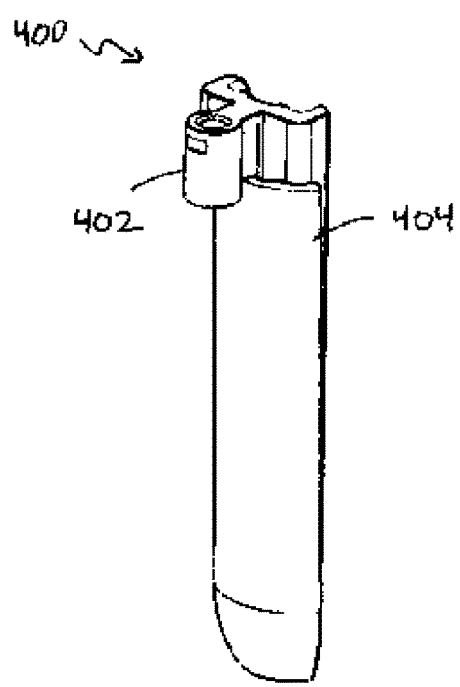
FIGS. 20A-21C illustrate a blade for a spinal retractor according to one embodiment.
Figure 20B:
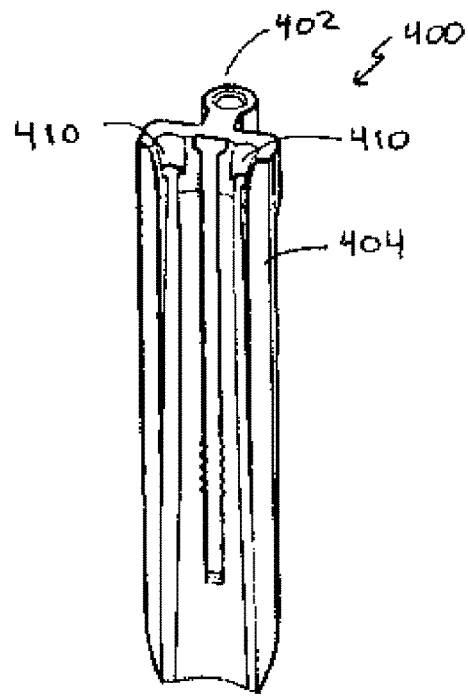
Figure 21A:
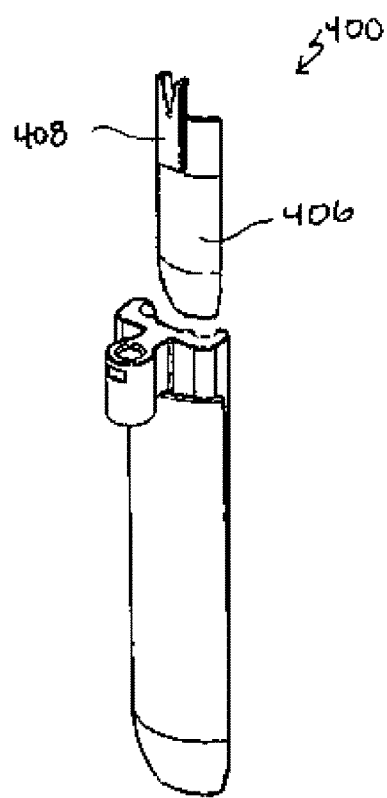
Figure 21B:
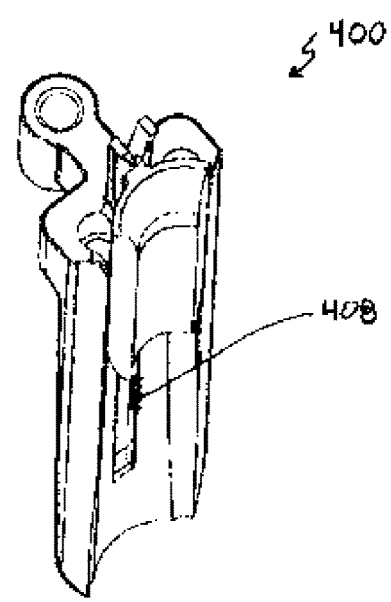
Figure 21C:
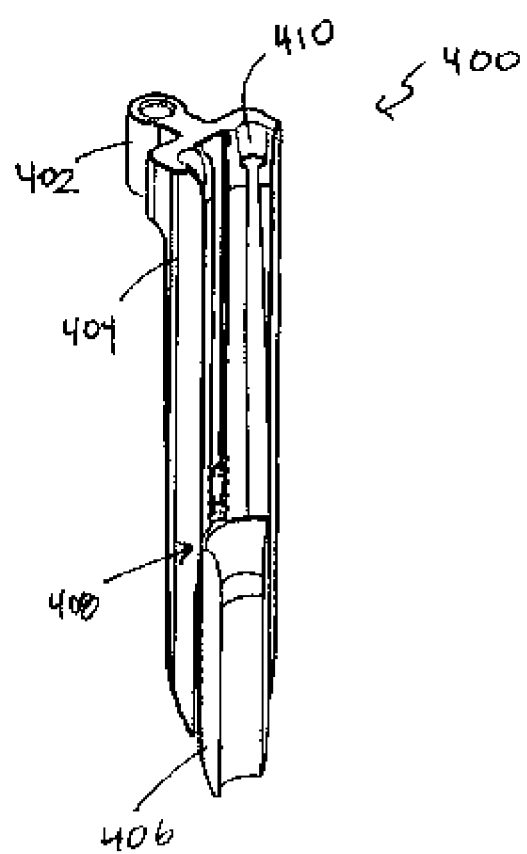

Referring now to FIG. 17, in one embodiment, blade assemblies 282, 316, 342 form a circular interior when spinal retractor 210 is in the closed position and blade assemblies 282, 316, and 342 are in a non-angulated orientation. Dependent upon a desired type and degree of distraction, the various side and center assemblies and blade assemblies may be moved to desired positions to provide the desired retraction for a particular procedure.

Referring to FIGS. 20A-21C, a blade assembly 400 is shown according to an alternative embodiment. The features of blade assembly 400 may be implemented with any of blade assemblies 282, 316, and 342. In one embodiment, blade assembly 400 includes a blade support 402 coupled to a primary blade 404. A secondary blade 406 is removably and adjustably coupled to primary blade 404 via a ratchet mechanism 408. One or more channels 410 may be provided in primary blade 404 to enable insertion of light sources, fixation pins, or other components. For example, in some embodiments, upon positioning blade assembly 400 in a desired retraction position, one or more fixation pins may be placed within channel 410 to secure the blade(s) in place. Use of secondary blade 406 is in some embodiments optional, and enables, for example, prevention of tissue creep during procedures and eliminated the need to change to a longer blade during a procedure.

In use, spinal retractor 210 is positioned at a desired position relative to a patient, and may be secured using one or more of table arm mounts 228, 230, 231. Spinal retractor 210 is normally initially in a closed configuration (see, e.g., FIG. 11). Spinal retractor may be moved to a desired open configuration by translating one or more of first side assembly 214, second side assembly 216, and center assembly 218 relative to base 212. Further, one or more of blade assemblies 282, 316, or 342 (or similarly, blade assembly 400), may be angulated into a desired position of angulation. In some embodiments, a secondary blade may be utilized to prevent tissue creep during a procedure, and one or more components (e.g., lights, fixation pins, etc.) may be utilized via one or more of the blade assemblies.

Referring now to FIGS. 22-32C, a spinal retractor 510 is shown according to another alternative embodiment. The spinal retractor 510 shown in FIGS. 22-30 shares many of the features of the spinal retractors shown in FIGS. 1-5 and 6-21, and all such features are understood to be part of the embodiment shown in FIGS. 22-30.

Figure 22:
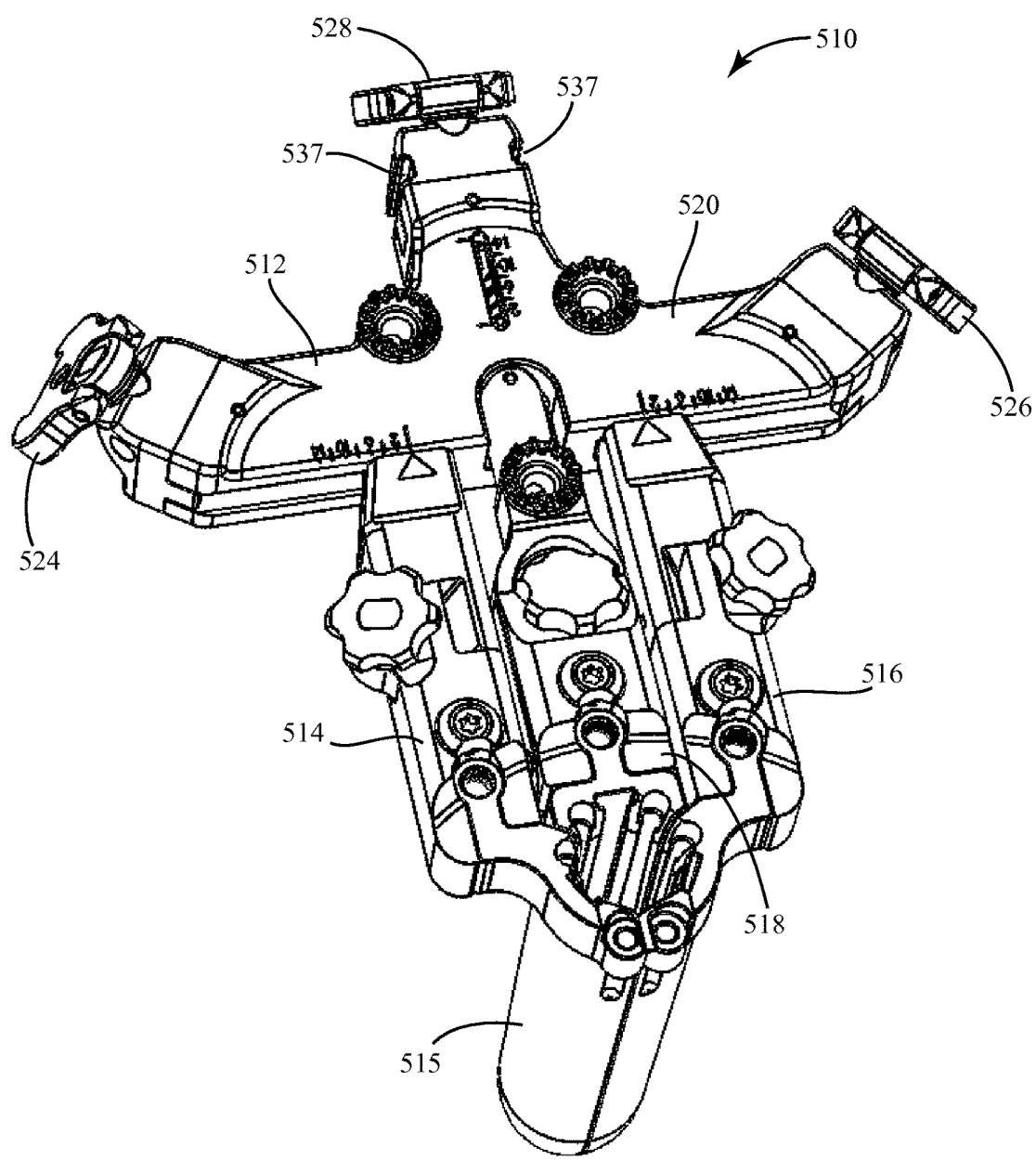
FIG. 22 is a perspective view of a spinal retractor according to another embodiment.
Figure 23:
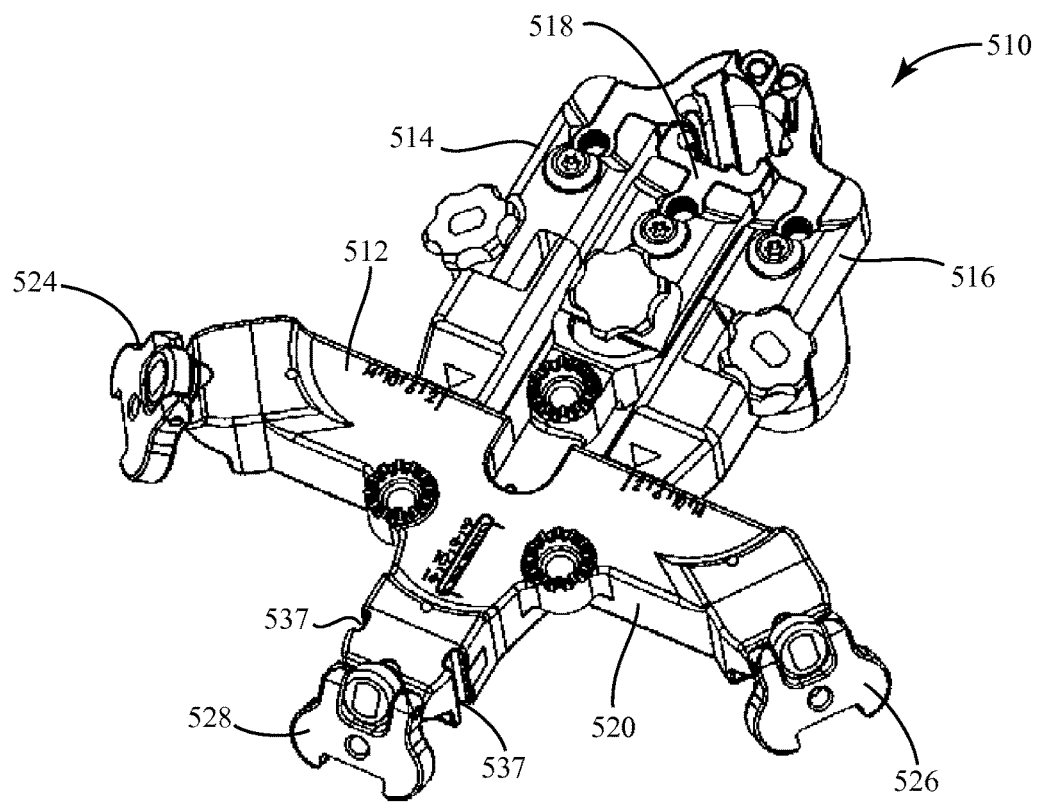
FIGS. 23-24 are additional perspective views of the spinal retractor of FIG. 22 according to one embodiment.
Figure 24:
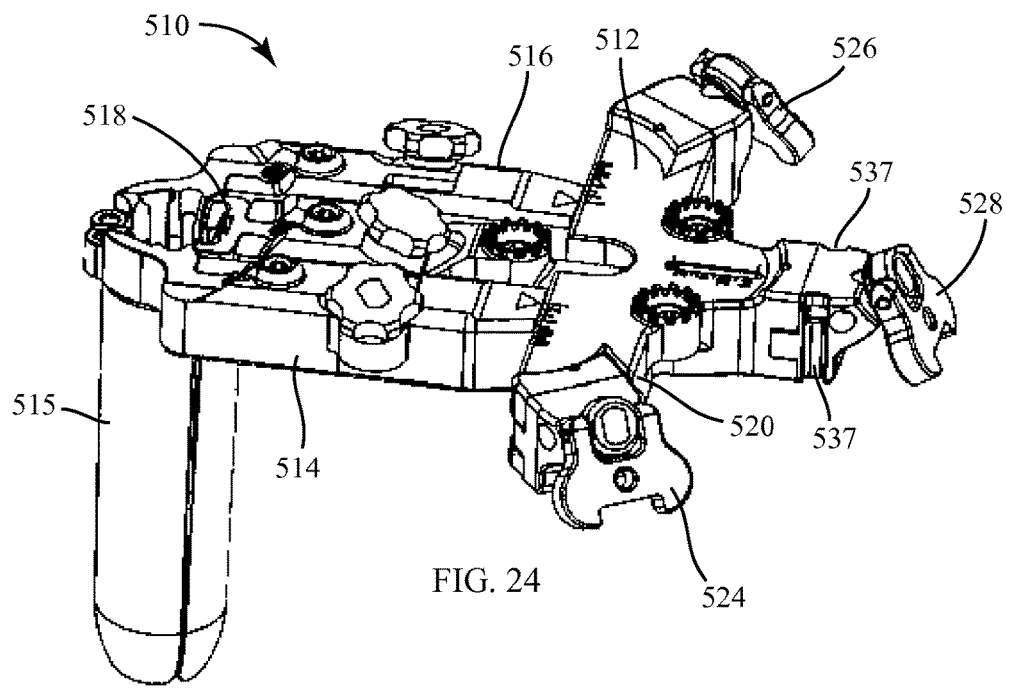

Referring to FIGS. 22-24, the spinal retractor 510 includes a frame or base 512, a first side assembly 514, a second side assembly 516, and a center assembly 518. The first side assembly 514, the second side assembly 516, and the center assembly 518 are coupled to the base 512 to enable translating movement of the assemblies 514, 516, and 518 relative to the base 512 to provide retraction of tissue, etc. during surgical procedures involving the spine, etc. The first side assembly 514 and the second side assembly 516 translate relative to the base 512 in a medial-lateral direction (e.g., along a first axis or direction), and the center assembly 518 translates relative to the base 512 in a cephalad-caudal direction (e.g., along a second axis or direction) in a generally perpendicular fashion relative to the first and second side assemblies. In one embodiment, each of the assemblies 514, 516, 518 may be adjusted (e.g., translated) relative to the base 512 independently (e.g., such that each of the first side assembly 514, the second side assembly 516, and the center assembly 518 may be adjusted individually).

The base 512 includes a body 520, a first side adjustment knob or member 524, a second side adjustment knob or member 526, and a center adjustment knob or member 528. The first side adjustment knob 524 is operatively coupled to the first side assembly 514, the second side adjustment knob 526 is operatively coupled to the second side assembly 516, and the center adjustment knob 528 is operatively coupled to the center assembly 518, such that adjustment of knobs 524, 526, 528 causes a corresponding translational movement of the assemblies 514, 516, 518.

Figure 25:
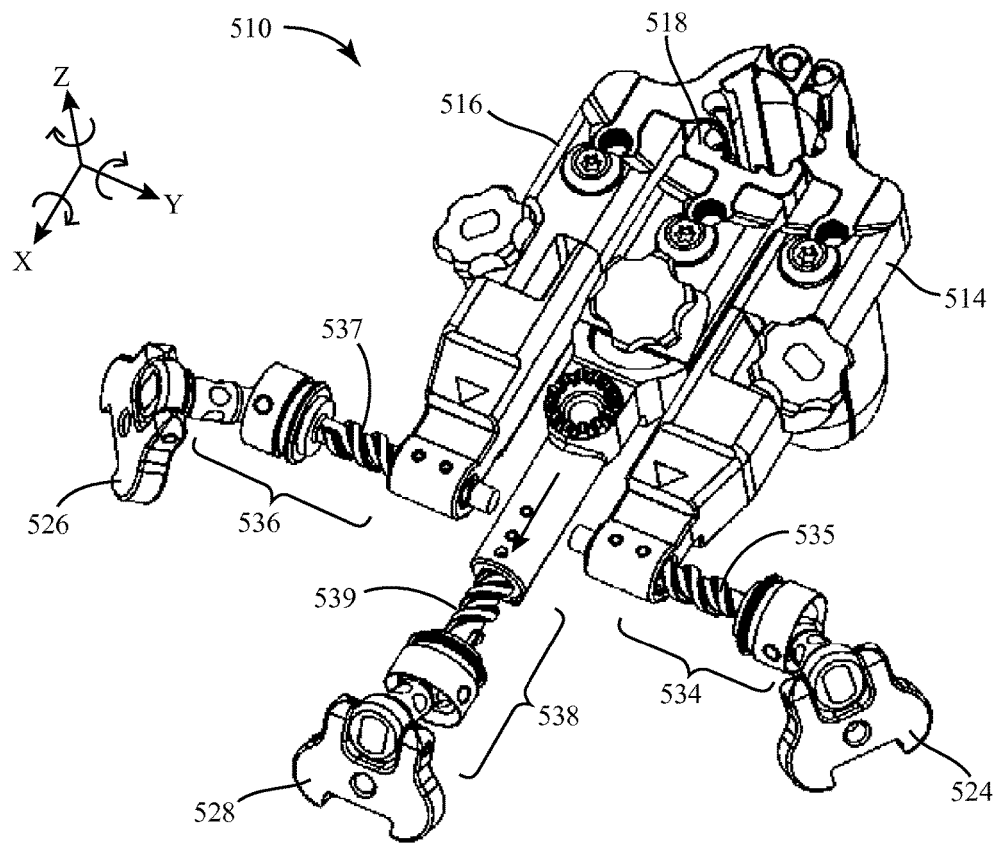
FIGS. 25-26 are perspective views of portions of the spinal retractor of FIG. 22 according to one embodiment.
Figure 26:
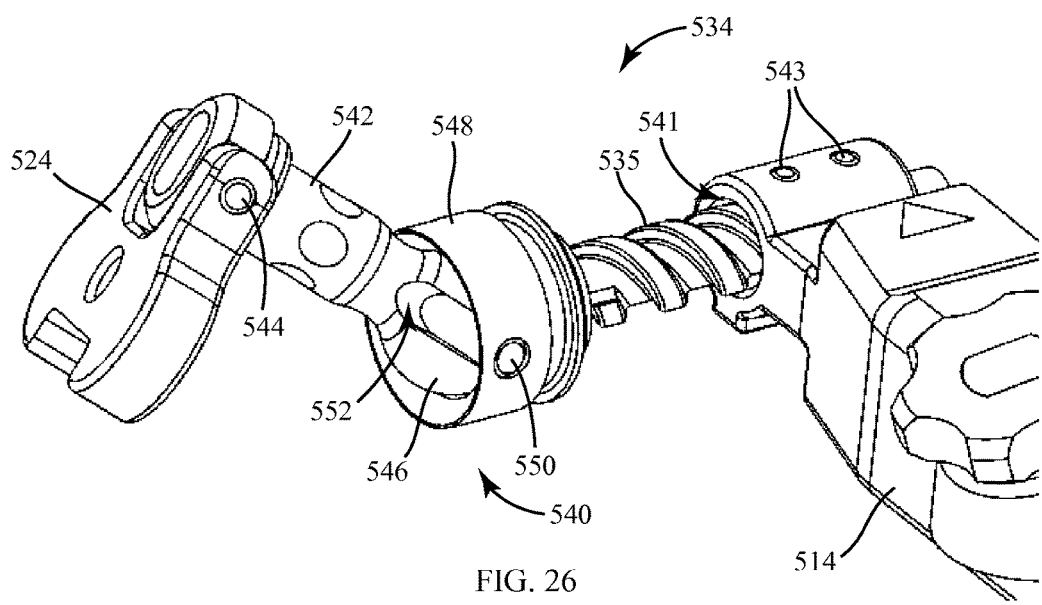

Referring to FIGS. 25-26, the first side adjustment knob 524 is coupled to a first threaded shaft 535 via a first side drive assembly 534, the second side adjustment knob 526 is coupled to a second threaded shaft 537 via a second side drive assembly 536, and the center adjustment knob 528 is coupled to a third threaded shaft 539 via a center drive assembly 538. The first side drive assembly 534, second side drive assembly 536, and center drive assembly 538 are similar in structure and function, and therefore only first side drive assembly 534 will be discussed in detail with respect to FIG. 26. However, it should be understood that any features shown and described with respect to the first side drive assembly 534 are equally applicable to the second side drive assembly 536 and the center drive assembly 538.

As shown in FIG. 26, the first side drive assembly 534 is operatively coupled to the first threaded shaft 535 via a first multi-axis joint assembly, shown as ball joint assembly 540. The first threaded shaft 535 is received in a bore 541 in the first side assembly 514. The first threaded shaft 535 engages one or more elements, shown as pins 543, that extend into the bore 541. Through the interaction between the pins 543 and the first threaded shaft 535, the first threaded shaft 535 advances into or withdraws from the bore 541 as the first threaded shat 535 is rotated. In other embodiments, the first threaded shaft 535 may otherwise engage the bore 541 in the first side assembly 514. For example, the bore 541 may be formed with an internal thread configured to engage the first threaded shaft 535.

The ball joint assembly 540 includes a drive shaft 542 pivotally coupled at a first end to the first side adjustment knob 524 by a pivot pin 544. The second end of the drive shaft 542 is in the form of a ball 546 that is adjustably coupled to a receiver 548 via a cross pin 550. The ball 546 defines a slot 552 sized to receive the cross pin 550 such that the drive shaft 542 can pivot about multiple axes (e.g., such that the first end of the drive shaft 542 is rotatable through a semi-spherical range of motion). For example, in a non-rotated position, the drive shaft 542 extends generally collinearly with the first threaded shift 535. When put into the position shown in FIG. 25, the drive shaft 542 is able to rotate about both the X-axis 554 and the Z-axis 556 shown in FIG. 25. Providing an angular offset for the drive shaft 542, and in turn, the first side adjustment knob 524, may provide a more advantageous position for adjusting the spinal retractor 510. In some embodiments, the first side drive assembly 534 is operatively coupled to the first threaded shaft 535 via another moveable coupling member that allows the drive shaft 542 to pivot about multiple axes (e.g., such that the first end of the drive shaft 542 is rotatable through a semi-spherical range of motion). For example, in some embodiments, the first side drive assembly 534 may be operatively coupled to the first threaded shaft 535 via a universal joint mechanism. Other types of multi-axis joints or coupling mechanisms may be used according to various alternative embodiments.

The spinal retractor 510 is movable between a closed configuration, shown in FIG. 22, to an open configuration, through translation of the first side assembly 514 and the second side assembly 516 and/or the center assembly 518 relative to the body. Furthermore, the first side assembly 514, the second side assembly 516, and the center assembly 518 receive blade assemblies 515, which are configured to hold tissue apart during various procedures. The blade assemblies 515 may be angulated (e.g., moved from a generally vertical orientation to one or more non-vertical, or angled, orientations) to suit a particular procedure. The first and second side assemblies and the center assembly may further include first and second portions such as those described with respect to FIGS. 15A-16B to provide further adjustment capabilities for the spinal retractor 510.

Figure 27:
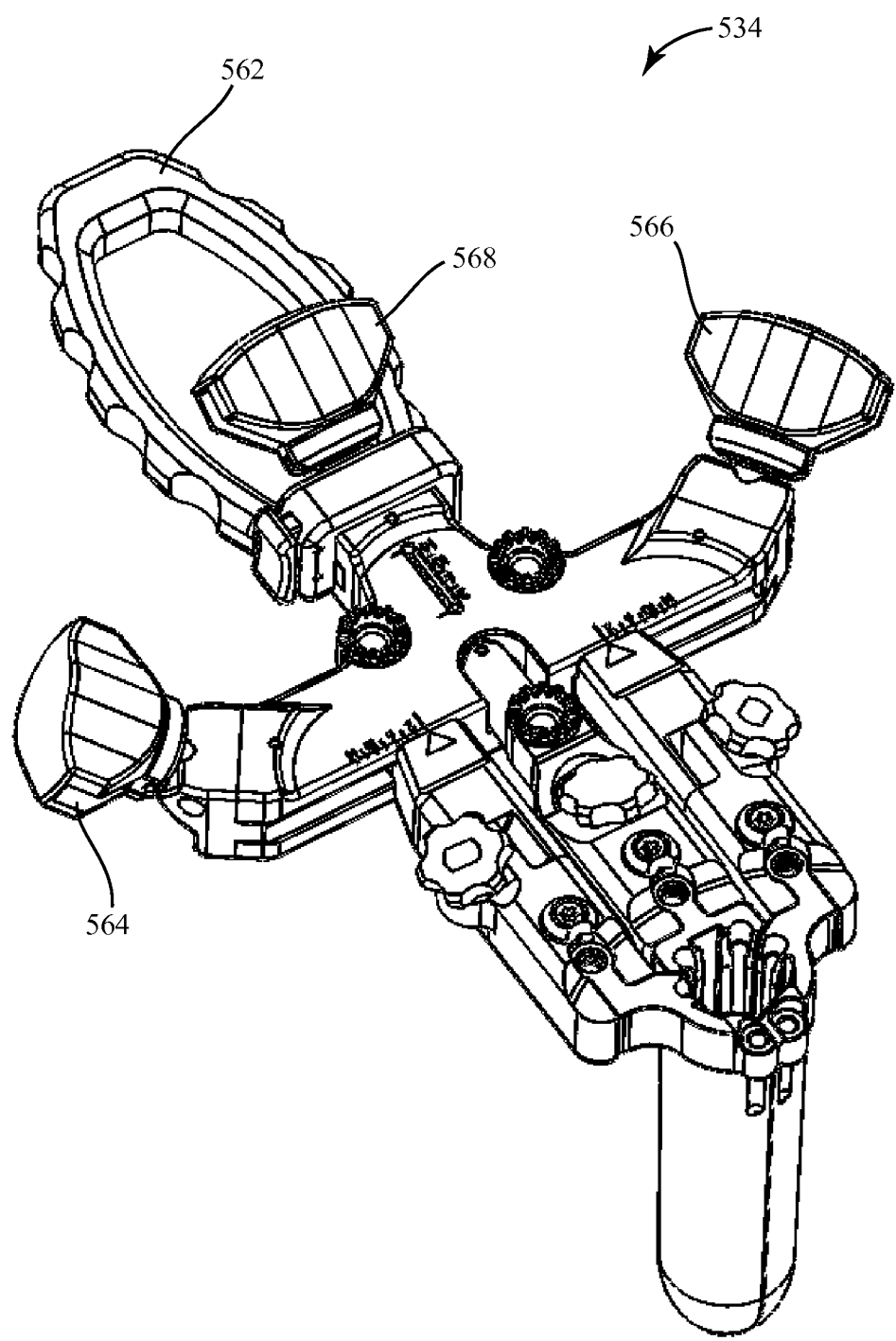
FIG. 27 is a perspective view of the spinal retractor of FIG. 22 with various handles attached according to one embodiment.

Referring now to FIGS. 27-30, the spinal retractor 510 is shown coupled to one or more handles. For example, as shown in FIG. 27, a first adjustment handle 564 is coupled to the first side adjustment knob 524, a second adjustment handle 566 is coupled to the second side adjustment knob 526, a third adjustment handle 568 is coupled to the center adjustment knob 528, and a support handle 562 is coupled to the base 512. The various handles are in one embodiment attached in a removable fashion such that the handles can be selectively attached/detached during use of the spinal retractor 510.

Figure 28:
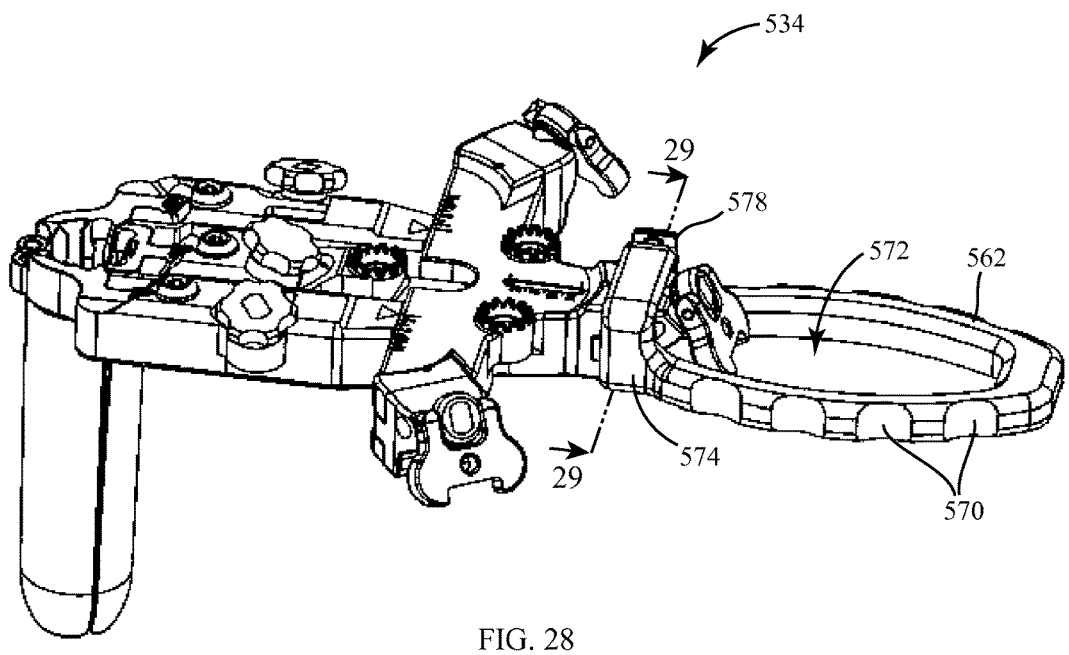
FIG. 28 is a perspective view of the spinal retractor of FIG. 22 with a support handle attached according to one embodiment.
Figure 29:
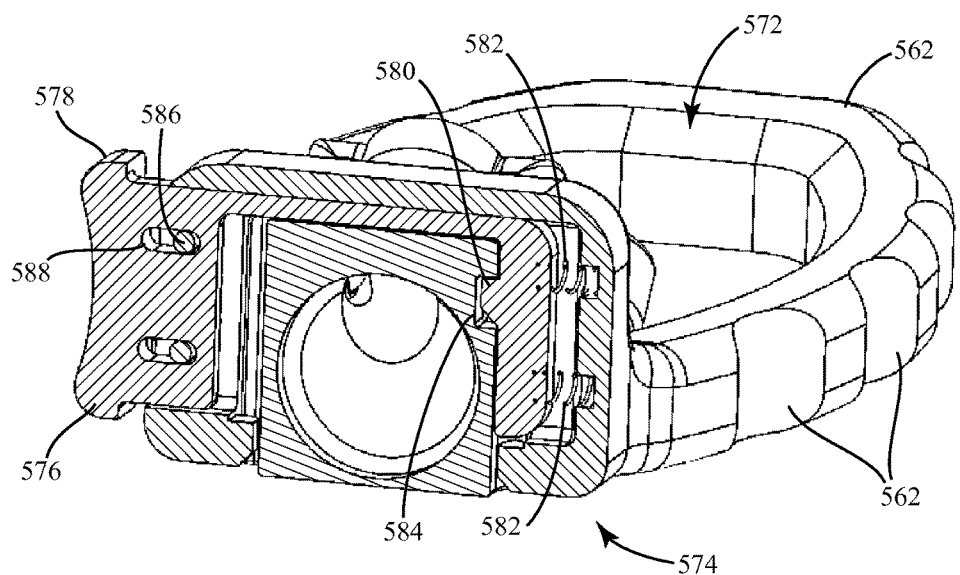
FIG. 29 is a perspective cross-sectional view of the spinal retractor of FIG. 22 taken along line A-A of FIG. 28 according to one embodiment.

As shown in FIGS. 28 and 29, the support handle 562 is coupled to the base 512 adjacent the center adjustment knob 528. The support handle 562 defines a plurality of grip portions 570 and a central aperture 572. In one embodiment, the support handle 562 is a substantially rigid member, while in alternative embodiments, the support handle 562 is a flexible and/or compressible member (e.g., such that the opposing sides of the support handle 562 are deformable inward toward each other). In some embodiments, the grip portions 570 are shaped to generally correspond to the shapes of the fingers of a user to prevent slippage between the spinal retractor and a hand of a user.

Referring to FIG. 29, in one embodiment, the support handle 562 includes a handle attachment portion 574 that is received in a groove 275 in the base 512 (see FIG. 22). As such, the support handle 562 may be slidably attached and detached relative to the base 512. As shown in FIG. 29, the attachment portion 574 includes a locking plate 576 defining a button 578 and projection 580. The locking plate 576 is received by the groove 275, and a pair of springs 582 bias the projection 580 into a recess 584 formed in the base 512 (e.g., as part of the groove 275). A pair of guide pins 586 received in slots 588 in the locking plate 576 maintain proper alignment of the locking plate 576. Depression of the button 578 disengages the projection 580 from the recess 584 and enables detachment of the support handle 562 from the base 512.

Figure 30:
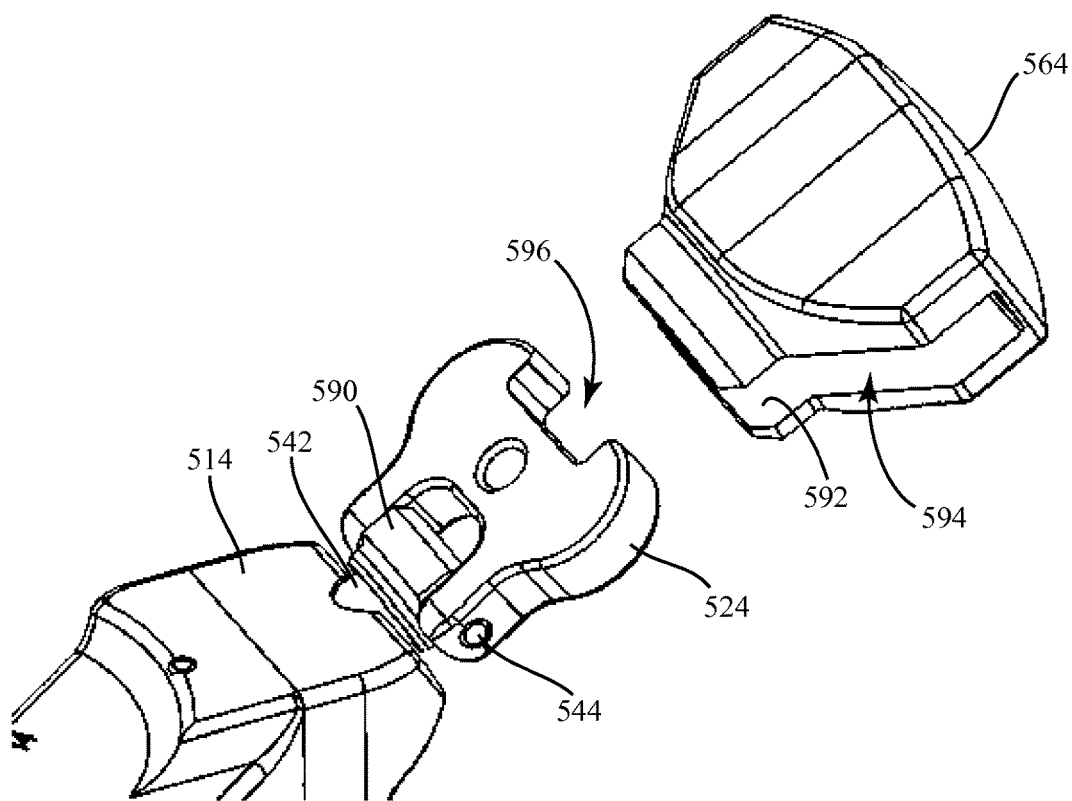
FIG. 30 is an exploded view of a portion of a spinal retractor according to one embodiment.
Figure 31A:
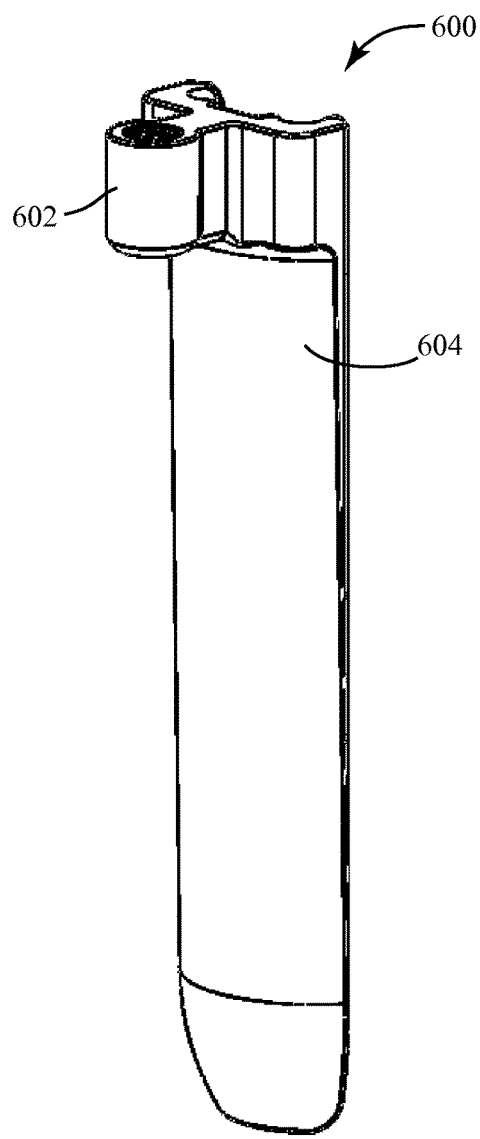
Figure 31B:
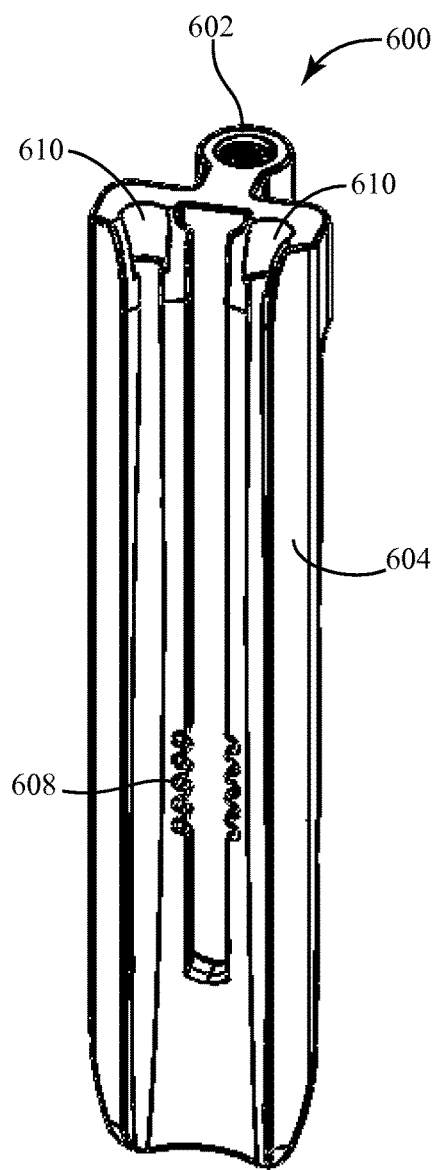

Referring to FIG. 30, the first adjustment handle 564 is shown removed from the first side adjustment knob 524. When the first adjustment handle 564 is detached, the first side adjustment knob 524 is free to rotate about the pivot pin 544. When the first adjustment handles 564 is attached, one or more flat portions 590 on the drive shaft 542 interface one or more flat portions 592 on the first adjustment handle 564 to resist rotation of the first side adjustment knob 524 relative to the drive shaft 542. In one embodiment, when the first adjustment handle 564 is coupled to the first side adjustment knob 524, the first adjustment handle 564 extends in a direction generally collinear with the axis of the drive shaft 542. In other embodiments, the first adjustment handle 564 may extend in other directions. The first adjustment handle 564 defines a slot 594 in which the first side adjustment knob 524 is received. A protrusion within the slot 594 engages a corresponding channel 596 to align the first adjustment handle 564 with the first side adjustment knob 524 and limits the movement of the first adjustment handle 564 with respect to the first side adjustment knob 524.

Referring to FIGS. 31A-32C, a blade assembly 600 is shown according to one embodiment. The blade assembly 600 may be similar in construction and features to the blade assembly 400 and may be implemented with any of blade assemblies 282, 316, 342, and 400. In one embodiment, blade assembly 600 includes a blade support 602 coupled to a primary blade 604. A secondary blade 606 is removably and adjustably coupled to primary blade 604 via a ratchet mechanism 608 (e.g., using one or more projections that are biased into one or more recesses to provide adjustable positioning of the secondary blade 606). One or more channels 610 may be provided in primary blade 604 to enable insertion of light sources, fixation pins, or other components. For example, in some embodiments, upon positioning blade assembly 600 in a desired retraction position, one or more fixation pins may be placed within channel 610 to secure the blade(s) in place. Use of secondary blade 606 is in some embodiments optional, and enables, for example, prevention of tissue creep during procedures and eliminated the need to change to a longer blade during a procedure.

It should be understood that the spinal retractor shown in FIGS. 22-30 may share any or all of the features described elsewhere herein, including blade extenders/supplemental blades, blade locking features, lighting features extending within channels in the blades, and the like. All such combinations of features are to be understood to be within the scope of the present disclosure.

In one embodiment, in operating a spinal retractor such as one described herein, the retractor is placed into a desired position. A first side assembly, a second side assembly, and a center assembly of the retractor are translated along threaded shafts relative to a frame of the retractor. The side and center assemblies may be translated via manipulation of ball joint assemblies that couple adjustment knobs to the respective threaded shafts.

The spinal retractor shown and described herein may provide various benefits over more traditional designs. The support handle provides a modular, ergonomic handle for improved manipulation of the base or frame to ease alignment of the device, and the adjustment handles provide modular ergonomic handles for translation of the side and center assemblies without the need for additional instrumentation. Further, the adjustment handles stabilize the positions of the adjustment knobs for ease of use. The gear rations of the threaded shafts provide faster translation of components (e.g., twice as fast as certain conventional device) such that each of the side and center assemblies can be completely expanded with 1.5 revolutions of the threaded shafts/adjustment knobs.

Additionally, the frame weight is less compared to more traditional devices (e.g., by 15 percent or more), and the frame geometry is optimized to enable table arm attachment to the center arm assembly while eliminating interference with the base or frame (e.g., in situations when the table arm extends generally parallel to the length of the frame or base). In some embodiments, blade extenders include self-retaining springs to ensure the blade extenders remain captured within the blades, and the blade locking mechanisms provide a spring-activated locking feature requiring only a one quarter turn to lock/unlock the blades. Further, light sources may extend down channels in the blades to provide optimized lighting (e.g., 15 percent or more light output relative to more traditional designs).

While the invention has been illustrated and described in detail in the drawings and foregoing description, the same is to be considered as illustrative and not restrictive in character, it being understood that only a preferred embodiment has been shown and described and that all changes and modifications that come within the spirit of the invention are desired to be protected.

What is claimed is:
1. A retractor assembly, comprising:
a base;
a first drive shaft at least partially received in the base;
a second drive shaft at least partially received in the base;
a third drive shaft at least partially received in the base;
a first threaded shaft disposed within the base;
a second threaded shaft disposed within the base;
a third threaded shaft disposed within the base;
a first side arm assembly coupled to a first side of the base and configured to translate relative to the base along a first direction based on rotation of the first drive shaft positioned in the base angularly offset at a first obtuse angle relative to the first direction, wherein the first side arm assembly translates along the first threaded shaft disposed within the base;
a second side arm assembly coupled to a second side of the base and configured to translate relative to the base along the first direction independent from the first side arm assembly and based on rotation of the second drive shaft positioned in the base angularly offset at a second obtuse angle relative to the first direction, wherein the second side arm assembly translates along the second threaded shaft disposed within the base;
a central arm assembly coupled to a central portion of the base between the first and second sides of the base and configured to translate relative to the base along a second direction different from the first direction based on rotation of the third drive shaft positioned in the base angularly offset at a third obtuse angle relative to the second direction, wherein the central arm assembly translates along the third threaded shaft disposed within the base;

a first adjustment knob coupled to the first drive shaft via a first pivot pin that permits relative pivotal rotation between the first adjustment knob and the first drive shaft, and the first drive shaft is operatively coupled to the first threaded shaft via a first multi-axis joint which allows relative pivotal rotation between the first drive shaft and the first threaded shaft about more than one axis;

a second adjustment knob coupled to the second drive shaft via a second pivot pin that permits relative pivotal rotation between the second adjustment knob and the second drive shaft, and the second drive shaft is operatively coupled to the second threaded shaft via a second multi-axis joint which allows relative pivotal rotation between the second drive shaft and the second threaded shaft about more than one axis;

a third adjustment knob coupled to the third drive shaft via a third pivot pin that permits relative pivotal rotation between the third adjustment knob and the third drive shaft, and the third drive shaft is operatively coupled to the third threaded shaft via a third multi-axis joint which allows relative pivotal rotation between the third drive shaft and the third threaded shaft about more than one axis;

at least one adjustment handle removably attachable to at least one of the first adjustment knob, the second adjustment knob, and the third adjustment knob;

a support handle removably coupled to the base and extending along the second direction, wherein the base includes an attachment groove slidably receives an attachment portion of the support handle, and wherein the attachment portion of the support handle includes a spring-biased locking plate having a projection releasably engages a recess provided on the base for removably coupling said support hand to said base; and wherein the central arm assembly, when coupled to the third threaded shaft within the central portion of the base, extends from the base in a generally parallel fashion relative to both the first side arm assembly and the second side arm assembly, when coupled to the first and second threaded shafts within the first and second sides of the base, respectively.

2. The retractor assembly of claim 1, wherein the at least one adjustment handle includes:
 a first adjustment handle removably attachable to the first adjustment knob;
 a second adjustment handle removably attachable to the second adjustment knob; and
 a third adjustment handle removably attachable to the third adjustment knob.

3. The retractor assembly of claim 1,
 wherein each of the first, second, and third multi-axis joints includes at least one of a ball joint and a universal joint.

4. The retractor assembly of claim 1, wherein the support handle comprises a plurality of gripping members extending about at least a portion of the periphery of the support handle and an interior portion defining a handle aperture.

5. The retractor assembly of claim 1, wherein the locking plate defines a button pressable to move the projection out of engagement with the recess, and wherein the locking plate remains coupled to a remainder of the handle as the button is pressed and released and as the handle engages and disengages the base.

6. A retractor assembly, comprising:
 a base;
 a first side arm assembly coupled to a first side of the base and configured to translate relative to the base along a first direction;
 a second side arm assembly coupled to a second side of the base and configured to translate relative to the base along the first direction independent from the first side arm assembly; and
 a central arm assembly coupled to a central portion of the base between the first and second sides of the base and configured to translate relative to the base along a second direction different from the first direction;
 each of the first side arm assembly, the second side arm assembly, and the center arm assembly is coupled to the base by an adjustment mechanism including a multi-axis joint assembly;
 the adjustment mechanism includes a threaded shaft disposed within the base, wherein the multi-axis joint assembly includes a drive shaft coupled to the threaded shaft via a ball received within a receiver, and a cross-pin extends through a slot in the ball and into the receiver to rotatably couple the ball to the receiver, so as to allow relative pivotal rotation between the drive shaft and the threaded shaft about more than one axis, and wherein the drive shaft is positioned in the base at an obtuse angle relative to the threaded shaft, and wherein the adjustment mechanism further includes an adjustment knob coupled to the drive shaft via a pivot pin; and an adjustment handle removably coupled to the adjustment knob;
 wherein rotation of a first drive shaft of the adjustment mechanism about its longitudinal axis causes rotation of a first threaded shaft of the adjustment mechanism about its longitudinal axis within the base to cause the first arm assembly to translate along the first threaded shaft relative to the base in the first direction,
 wherein rotation of a second drive shaft of the adjustment mechanism about its longitudinal axis causes rotation of a second threaded shaft of the adjustment mechanism about its longitudinal axis within the base to cause the second arm assembly to translate along the second threaded shaft relative to the base in the first direction,
 wherein rotation of a third drive shaft of the adjustment mechanism about its longitudinal axis causes rotation of a third threaded shaft of the adjustment mechanism about its longitudinal axis within the base to cause the third arm assembly to translate along the third threaded shaft relative to the base in the second direction, and
 a support handle removably coupled to the base and extending along the second direction, wherein the base includes an attachment groove slidably receives an attachment portion of the support handle, and wherein the attachment portion of the support handle includes a spring-biased locking plate having a projection releasably engages a recess provided on the base for removably coupling said support hand to said base; and
 wherein the central arm assembly, when coupled to the third threaded shaft within the central portion of the base, extends from the base in a generally parallel fashion relative to both the first side arm assembly and the second side arm assembly, when coupled to the first and second threaded shafts within the first and second sides of the base, respectively.

7. The retractor assembly of claim 6, wherein the first, second and third threaded shafts are rotatable relative to the base and translationally fixed relative to the base.

* * * * *